US009556235B2

(12) United States Patent
Kornecki et al.

(10) Patent No.: US 9,556,235 B2
(45) Date of Patent: *Jan. 31, 2017

(54) F11 RECEPTOR (F11R) ANTAGONISTS AS THERAPEUTIC AGENTS

(71) Applicants: Elizabeth Kornecki, Christiansted, VI (US); Anna Babinska, Staten Island, NY (US); Yigal H. Ehrlich, Christiansted, VI (US); Moro Salifu, Brooklyn, NY (US)

(72) Inventors: Elizabeth Kornecki, Christiansted, VI (US); Anna Babinska, Staten Island, NY (US); Yigal H. Ehrlich, Christiansted, VI (US); Moro Salifu, Brooklyn, NY (US)

(73) Assignee: The Research Foundation for The State University of New York, Albany, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/052,147

(22) Filed: Oct. 11, 2013

(65) Prior Publication Data

US 2014/0155576 A1 Jun. 5, 2014

Related U.S. Application Data

(60) Division of application No. 13/156,883, filed on Jun. 9, 2011, now Pat. No. 8,557,957, which is a continuation-in-part of application No. 12/358,352, filed on Jan. 23, 2009, now abandoned, which is a continuation-in-part of application No. 12/141,635, filed on Jun. 18, 2008, now Pat. No. 7,829,663, which is a division of application No. 11/173,037, filed on Jul. 1, 2005, now abandoned, which is a continuation-in-part of application No. PCT/US03/39890, filed on Dec. 16, 2003.

(60) Provisional application No. 60/438,669, filed on Jan. 3, 2003.

(51) Int. Cl.

| C07K 14/00 | (2006.01) |
| C07K 14/705 | (2006.01) |
| C07K 7/06 | (2006.01) |
| C07K 7/08 | (2006.01) |
| C07K 7/02 | (2006.01) |
| C07K 5/10 | (2006.01) |
| A61K 38/00 | (2006.01) |

(52) U.S. Cl.
CPC ............. C07K 14/00 (2013.01); C07K 5/10 (2013.01); C07K 7/02 (2013.01); C07K 7/06 (2013.01); C07K 7/08 (2013.01); C07K 14/70503 (2013.01); *A61K 38/00* (2013.01)

(58) Field of Classification Search
CPC ... A61K 38/00; C07K 14/00; C07K 14/70503; C07K 7/08; C07K 7/06; C07K 5/10
See application file for complete search history.

(56) References Cited

U.S. PATENT DOCUMENTS

| 4,946,778 | A | 8/1990 | Ladner et al. |
| 5,051,448 | A | 9/1991 | Shashoua |
| 5,169,862 | A | 12/1992 | Burke, Jr. et al. |
| 5,192,746 | A | 3/1993 | Lobl et al. |
| 5,359,046 | A | 10/1994 | Capon et al. |
| 5,539,085 | A | 7/1996 | Bischoff et al. |
| 5,559,103 | A | 9/1996 | Gaeta et al. |
| 5,576,423 | A | 11/1996 | Aversa et al. |
| 5,665,701 | A | 9/1997 | Kornecki et al. |
| 6,150,502 | A | 11/2000 | Strachan |
| 6,358,707 | B1 | 3/2002 | Gupta et al. |
| 6,699,688 | B1 | 3/2004 | Kornecki et al. |
| 2004/0115135 | A1 | 6/2004 | Quay |

FOREIGN PATENT DOCUMENTS

| EP | 0 045 665 | 2/1982 |
| EP | 0 125 023 | 11/1984 |
| EP | 0 173 494 | 3/1986 |
| EP | 0 184 187 | 6/1986 |
| EP | 0 171 496 | 11/2011 |
| WO | 86/01533 | 3/1986 |
| WO | 87/02671 | 5/1987 |
| WO | 99/02561 | 1/1999 |
| WO | 2004/063327 | 7/2004 |

OTHER PUBLICATIONS

Karsan A. et al., "The Blood Vessel Wall", In Hematology: Basic Principles and Practice, 3rd Ed. 1770-1782 (2000).
Cines D.B. et al., "Endothelial Cells in Physiology and in the Pathophysiology of Vascular Disorders", Blood 91(10):3527-3561 (1998).
May A.E. et al., "The Relevance of Blood Cell-Vessel Wall Adhesive Interactions for Vascular Thrombotic Disease", Thrombosis and Haemostasis 82(2):962-970 (1999).
Diquélou A. et al., "Relationship Between Endothelial Tissue Factor and Thrombogenesis Under Blood Flow Conditions", Thrombosis and Haemostasis 74(2):778-783 (1995).
Dardik R. et al., "Recombinant Fragment of Von Willebrand Factor AR545C Inhibits Platelet Binding to Thrombin and Platelet Adhesion to Thrombin-Treated Endothelial Cells", British Journal of Haematology 109:512-518 (2000).
André P. et al., "Platelets Adhere to and Translocate on Von Willebrand Factor Presented by Endothelium in Stimulated Veins", Blood 96(10):3322-3328 (2000).
Rosenblum W.I. et al., "Role of Platelet-Endothelial Cell Adhesion Molecule (PECAM) in Platelet Adhesion/Aggregation Over Injured but Not Denuded Endothelium In Vivo and Ex Vivo", Stroke 27(4):709-711 (1996).

(Continued)

*Primary Examiner* — Robert Landsman
*Assistant Examiner* — Bruce D Hissong
(74) *Attorney, Agent, or Firm* — Scully, Scott, Murphy & Presser, P.C.

(57) ABSTRACT

The present invention provides a compound including a peptidomimetic which interacts sterically with the binding site of a F11R molecule, the peptidomimetic including a peptidomimetic having the SEQ ID NO: 4D. The present invention also provides a method for treating a disorder comprising administering peptide 4D to a mammal.

1 Claim, 20 Drawing Sheets

(56) References Cited

OTHER PUBLICATIONS

Bombeli T. et al., "Adhesion of Activated Platelets to Endothelial Cels: Eidence for a GPIIb-IIa-Dependent Bridging Mechanism and Novel Roles for Endothelial Intercellular Adhesion Molecule I (ICAM-1) αvβ3 Integrin, and GPIbα", J. Exp. Med. 187(3):329-339 (1998).

Verheul H.M.W. et al., "Vascular Endothelial Growth Factor-Stimulated Endothelial Cells Promote Adhesion and Activation of Platelets", Blood 96(13):4216-4221 (2000).

Kornecki E. et al., "Activation of Human Platelets by a Stimulatory Monoclonal Antibody", The Journal of Biological Chemistry 265(17):10042-10048 (1990).

Naik U.P. et al., "Mechanisms of Platelet Activation by a Stimulatory Antibody: Cross-Linking of a Novel Platelet Receptor for Monoclonal Antibody F11 with the FcγRII Receptor", Biochem. J. 310:155-162 (1995).

Martin-Padura I. et al., "Junctional Adhesion Molecule, a Novel Member of the Immunoglobulin Superfamily that Distributes at Intercellular Junctions and Modulates Monocyte Transmigration", The Journal of Cell Biology 142(1):117-127 (1998).

Kornecki E. et al., "Identification of a Unique Type of Thrombopathy of Human Platelets: Defect in the Exposure of Active Fibrinogen Receptors in a Patient with Friedreich's Atxaxia", J. Lab Cln. Med. 111:618-626 (1988).

Wang F. et al., "Stimulatory Antibody-Induced Activation and Selective Translocation of Protein Kinase C Isoezymes in Human Platelets", Biochem. J. 311:401-406 (1995).

Sobocka M. et al., "Molecular Mechanisms of Platelet Activation by a Stimulatory Monoclonal Antibody, Cloning and Potential Pathophysiological Roles for a Novel Platelet Receptor", Blood 90(10), Supplement 1 (part 2 of 2):2996 (1997).

Sobocka M.B. et al., "Cloning of the Human Platelet F11 Receptor: A Cell Adhesion Molecule Member of the Immunoglobulin Superfamily Involved in Platelet Aggregation", Blood 95(8):2600-2609 (2000).

Babinska A. et al., "Two Regions of the Human Platelet F11-Receptor (F11R) Are Critical for Platelet Aggregation, Potentiation and Adhesion", Thromb Haemost 87:712-721 (2002).

Ozaki H et al., Cutting Edge: Combined Treatment of TNF-α and IFN-γ Causes Redistribution of Junctional Adhesion Molecule in Human Endothelial Cells, The Journal of Immunology 163:553-557 (1999).

Williams L.A. et al., "Identification and Characterisation of Human Junctional Adhesion Molecule (JAM)", Molecular Immunology 36:1175-1188 (1999).

Liu Y. et al., "Human Junction Adhesion Molecule Regulates Tight Junction Resealing in Epithelia", Journal of Cell Science 113:2363-2374 (2000).

Gupta S.K. et al., "Platelet Agonist F11 Receptor Is a Member of the Immunoglobulin Superfamily and Identical with Junctional Adhesion Molecule (JAM): Regulation of Expression in Human Endothelial Cells and Macrophages", IUBMB Life 50:51-56 (2000).

Naik U.P. et al., "Characterization and Chromosomal Localization of JAM-1, a Platelet Receptor for a Stimulatory Monoclonal Antibody", Journal of Cell Science 114(3):539-547 (2000).

Sobocka M.B. et al., "F11 Receptor-Mediated Potentiation of Platelet Activation by Subthreshold Concentrations of Physiological Agonists", XVIII Congress, Abstract #P1902 (2001).

Babine R.E. et al., "Molecular Recognition of Protein-Ligand Complexes: Applications to Drug Design", Chem. Rev. 97:1359-1472 (1997).

Hanessian S. et al., "Design and Synthesis of Conformationally Constrained Amino Acids as Versatile Scaffolds and Peptide Mimetics", Tetrahedron 53(37-39):12789-12854 (1997).

Fletcher M.D. et al., Partially Modified Retro-Inverso Peptides: Development, Synthesis, and Conformational Behavior, Chemical Reviews 98(2):763-795 (1998).

Morley J.S., "Modulation of the Action of Regulatory Peptides by Structural Modification", Trends Pharm. Sci. 463-468 (1980).

Hudson D. et al., "Methionine Enkephalin and Isosteric Analogues", Int. J. Peptide Protein Res. 14:177-185 (1979).

Spatola A.F. et al., "Structure-Activity Relationships of Enkephalins Containing Serially Replaced Thiomethylene Amide Bond Surrogates", Life Sciences 38(14):1243-1249 (1986).

Hann M.M. et al., "On the Double Bond Isostere of the Peptide Bond: Preparation of an Enkephalin Analogue", J. Chem. Soc. Perkin Trans. I, 307-314 (1982).

Almquist R.G. et al., "Synthesis and Biological Activity of a Ketomethylene Analogue of a Tripeptide Inhibitor of Angiotensin Converting Enzyme", Journal of Medicinal Chemistry 23(12):1392-1398 (1980).

Jennings-White C. et al., "Synthesis of Ketomethylene Analogs of Dipeptides", Tetrahedron Letters 23(25:2533-2534 (1982).

Holladay M. W. et al., "Synthesis of Hydroxyethylene and Ketomethylene Dipeptide Isosteres", Tetrahedron Letters 24(41):4401-4404 (1983).

Hruby V.J., "Conformational Restrictions of Biologically Active Peptides Via Amino Acid Side Chain Groups", Life Sciences 31(3):189-199 (1982).

Eldred C.D. et al., "Orally Active Non-Peptide Fibrinogen Receptor (GpIIb/IIIa) Antagonists: Identification of 4-[4-[4-(Aminoiminomethyl)phenyl]-1-piperazinly]-1-piperidineacetic Acid as a Long-Acting, Broad-Spectrum Antithrombotic Agent", Journal of Medicinal Chemistry 37(23):3882-3882 (1994).

Ku T.W. et al., "Potent Non-Peptide Fibrinogen Receptor Antagonists Which Present an Alternative Pharmacophore", Journal of Medicinal Chemistry 38(1):9-12 (1995).

Ferguson M.A.J. et al., "Cell-Surface Anchoring of Proteins Via Glycosyl-Phosphatidylinositol Structures", Ann. Rev. Biochem. 57:285-320 (1998).

Noren C.J. et al., "A General Method for Site-Specific Incorporation of Unnatural Amino Acids into Proteins", Science 244:182-188 (1989).

Farmer P.S., "Bridging the Gap Between Bioactive Peptides and Nonpeptides: Some Perspectives in Design", Drug Design (E.J. Ariëns, ed.) 10:119-143 (1980).

Ball J.B. et al., "Conformational Constraints: Nonpeptide β-Turn Mimics", Journal of Molecular REcognition 3(2):55-64 (1990).

Freidinger R.M., "Non-Peptide Ligands for Peptide Receptors", Trends Pharmacol. Sci. 10:270-274 (1989).

Merrifield R.B., "Solid Phase Peptide Synthesis I. The Synthesis of A Tetrapeptide", J. Am. Chem. Soc. 58:2149-2154 (1963).

Matteucci M.D. et al., "Synthesis of Deoxyoligonucleotides on a Polymer Support", J. Am. Chem. Soc. 103(11):3185-3191 (1981).

Bedzyk W.D. et al., "Immunological and Structural Characterization of a High Affinity Anti-Fluorescein Single-Chain Antibody", The Journal of Biological Chemistry 265(30):18615-18620 (1990).

Chaudhary V.K. et al., "A Recombinant Single-Chain Immunotoxin Composed of Anti-Tac Variable Regions and a Truncated Diphteria Toxin", Proc. Natl. Acad. Sci. USA 87:9491-9494 (1990).

Kohler et al., "Continuous Cultures of Fused Cells Secreting Antibody of Predefined Specificity", Nature 256:495-497 (1975).

Liu A.Y. et al., "Chimeric Mouse-Human IgG1 Antibody that Can Mediate Lysis of Cancer Cells", Proc. Natl. Acad. Sci. USA 84:3439-3443 (1987).

Sun L.K. et al., "Chimeric Antibody with Human Constant Regions and Mouse Variable Regions Directed Against Carcinoma-Associated Antigen 17-1A", Proc. Natl. Acad. Sci. USA 84:214-218 (1987).

Better M. et al., "*Escherichia coli* Secretion of an Active Chimeric Antibody Fragment", Science 240:1041-1043 (1988).

Tuszynski G.P. et al., "Spectrophotometric Quantitation of Anchorage-Dependent Cell Numbers Using the Bicinchoninic Acid Protein Assay Reagent", Analytical Biochemistry 184:189-191 (1990).

Kostrewa D. et al., "X-Ray Structure of Junctional Adhesion Molecule: Structural Basis for Homophilic Adhesion via a Novel Dimerization Motif", The EMBO Journal 20(16:4391-4398 (2001).

U.S. Office Action mailed Oct. 18, 2012 in related U.S. Appl. No. 13/156,883, filed Jun. 9, 2011.

1. Control (Non Fab added)
2. 100μg Fab added

1. Control (No Fab added)
2. 100 µg/ml Fab added
3. 200 µg/ml Fab added

Apo E-/- mouse 6.5 months old + P (5 months injection)

Apo E-/- mouse 6.5 months old

Apo E-/- 6.5 months old + P

Apo E-/- 6.5 months old

Apo E-/- 6.5 months old + P

Apo E-/- 6.5 months old

P1　　P2　　P3　　｜　H1　　H2　　｜　C1　　C2　　C3
　Peptide 4D　　　｜　Control (H₂O)　｜　　Control (--)

3 Months of injections

F11 RECEPTOR (F11R) ANTAGONISTS AS THERAPEUTIC AGENTS

CROSS REFERENCE TO RELATED APPLICATIONS

The present application is a divisional of U.S. Ser. No. 13/156,883 filed on Jun. 9, 2011, which is a Continuation-in-Part of U.S. Ser. No. 12/358,352 filed on Jan. 23, 2009, now abandoned, which is a Continuation-in-Part of U.S. Ser. No. 12/141,635 filed on Jun. 18, 2008, now U.S. Pat. No. 7,829,663 issued on Nov. 9, 2010, which is a divisional of U.S. Ser. No. 11/173,037, filed on Jul. 1, 2005, now abandoned, which was a Continuation-in-Part of PCT/US2003/39890, filed on Dec. 16, 2003, which claims the benefit of U.S. Provisional Application No. 60/438,669 filed on Jan. 3, 2003, the entire contents of which are incorporated herein by reference.

FIELD OF THE INVENTION

The present invention relates to protein and peptide chemistry, as well as crystallography and organic chemistry. The present invention is directed to a cell adhesion molecule (CAM) and fragments thereof, and more particularly to a CAM designated as the F11 receptor (F11R), or a polypeptide fragment thereof. The present invention also relates to F11R-antagonists and methods for the prevention and treatment of excessive bleeding following a wound injury, inflammatory diseases of the nervous system, thrombosis, inflammatory thrombosis, atherothrombosis, atherosclerosis, angiogenesis, plaque formation, cancer, immunothrombocytopenia (ITP), heart attacks, stroke, disorders of platelet and endothelial cell dysfunctions and other disorders involving thrombus formation, and hypertension.

BACKGROUND OF THE INVENTION

The vasculature is recognized as a dynamic metabolic organ that exists under normal physiological conditions in an intact, undisturbed state (Karsan, et al. *In: Hematology: Basic Principles and Practice,* 3rd Ed. Hoffman, et al. (eds) 2000; pp. 1770-82). Endothelial cells (EC), which line the exposed (luminal) surface of blood vessels, are normally not thrombogenic. That is, healthy EC do not attract or bind circulating platelets (Cines, et al. *Blood* 1998, 91: 3527-61; May, et al. *Thromb Haemost* 1999, 82: 962-70). It is well known that the physiological function of the endothelium is to facilitate blood flow by providing a highly thromboresistant surface to flowing blood that inhibits platelet adhesion and clotting (Cines, et al.). However, under inflammatory conditions, the nonthrombotic surface of EC can be transformed to a prothrombotic surface following exposure to cytokines (May, et al.; Diquelou et al. *Thromb Haemost* 1995, 74: 778-83), resulting in procoagulant activity and a predisposition to thrombosis (May, et al.; Dardik, et al. *Br J. Haematol.* 2000, 109:512-8; Andre, et al. *Blood* 2000, 96:3322-8). Indeed, the adhesion, accumulation and recruitment of non-stimulated platelets on cytokine-stimulated EC have been reported, with studies implicating the Platelet Endothelial Cell Adhesion Molecule-1 (PECAM-1; Rosenblum, et al. *Stroke* 1995, 27:709-11); beta 1 integrin (Bombeli et al. *J Exp. Med.* 1998, 187:329-39), von Willebrand factor (Dardik, et al.; Andre, et al.), and tissue factor (Verheul, et al. *Blood* 2000, 96:4216-21) in these processes. Thus, under inflammatory conditions, cytokines induce alterations in EC which result in the adhesion of non-stimulated platelets.

Recently, a novel adhesion protein of the immunoglobulin (Ig) superfamily has been described with properties indicating a potential triggering role in the pathogenesis of inflammatory thrombosis, atherosclerosis and other disorders involving thrombosis formation. This protein was identified first on the surface of human platelets and called the F11 receptor (F11R; Kornecki, et al. *J Biol Chem* 1990, 265: 10042-8; Naik, et al. *Biochem J* 1995, 311: 155-62), and then on the surface of murine endothelial and epithelial cells and called JAM/JAM-A (Martin-Padura, et al. *J. Cell Biol.* 1998, 142:117-27.).

The human platelet F11 receptor (F11R) is a surface glycoprotein duplex (32 and 35 kD at core protein: 29 kDa) member of the immunoglobulin superfamily. The F11R was first discovered as the target of a potent stimulatory monoclonal antibody, M.Ab.F11, that induces platelet secretion followed by aggregation (Kornecki, et al.; Naik, et al.; Kornecki, et al. *J Lab Clin. Med.* 1988, 111:618-26; Wang et al. *Biochem. J.* 1995, 311: 401-6; Kornecki, et al. In: Leukocyte Typing V. Schlossman, et al. (eds.) Oxford University Press 1195: 1241-3; Sobocka, et al. *Blood* 1997, 90: 10, Supplement 1, Part 2, Nov. 15, 2996a.; Sobocka, *Ph.D. Thesis,* 1998: SUNY Downstate, Brooklyn, N.Y., Presented Jun. 10, 1998; published Sep. 15, 1998; Sobocka, et al. *Blood* 2000, 95:2600-9; Babinska, et al. *Thromb Haemost* 2002, 87: 712-21). Signal transduction mechanisms for platelet secretion and aggregation induced by M.Ab.F11 following its initial binding to F11R include: crosslinking of the F11R to the FcγRII (Naik, et al.), activation and translocation of specific PKC isozymes (Wang, et al.), phosphorylation of the F11R through activation of PKC (Naik, et al.; Wang, et al.), phosphorylation of the F11R following induction of platelet aggregation by the physiological agonists thrombin and collagen and by M.Ab.F11 itself (Sobocka, et al. 1997; Sobocka; Sobocka, et al. 2000; Babinska, et al.), and phosphorylation of myosin light chain and pleckstrin, leading to shape change and granular secretion respectively (Kornecki, et al. 1990). Following secretion, this signal transduction pathway culminates in the activation of latent fibrinogen receptors and platelet aggregation (Kornecki, et al. 1990). Partial amino acid sequences representing 30% of the length of purified F11R have been reported by Kornecki in 1995 (Naik, et al.). Cloning of the full-length cDNA for the platelet F11R has revealed that it is a cell adhesion molecule (CAM), a member of the immunoglobulin superfamily (Sobocka, et al. 1997; Sobocka; Sobocka, et al. 2000). As a CAM, the F11R participates in mechanisms underlying adhesion of platelets, endothelial cells, and epithelial cells (Martin-Padura, et al.; Sobocka, et al. 2000).

The conclusion that, in addition to its role as a receptor that triggers signal transduction leading to secretion, the F11R also serves as a CAM involved in platelet adhesion was supported by the high degree of sequence similarity found between the human platelet F11R and an adhesion protein called Junctional Adhesion Molecule (JAM), a protein found in murine endothelial cells (Martin-Padura, et al. 1998). Comparison of the murine JAM sequence to the previously-reported sequences of the human platelet F11R (Naik, et al.) revealed over 70% homology of JAM to the N-terminus (23 amino acids) of F11R and to two enzyme-digested products of F11R. In addition, both the human platelet F11R core protein and the murine JAM protein were found to contain a single transmembrane domain and two pairs of cysteine residues in their extracellular domains that allow formation of intermolecular disulfide bridges forming characteristic Ig-like folds. It is now well established that the protein referred to as JAM (Martin-Padura, et al, 1998; Ozaki, et al. *J. Immunol.* 1999, 163: 553-7; Williams, et al. *Mol. Immunol.* 1999, 36: 1175-88; Liu, et al. *J. Cell Science* 2000, 113: 2363-74; Gupta, et al. *IUBMB Life* 2000, 50: 51-6; Naik, et al. *J. Cell Science* 2001, 114: 539-47), is the murine ortholog of the human F11R (Kornecki, et al. 1990; Naik, et al 1995; Kornecki, et al. 1988; Wang, et al.; Kornecki, et al 1995; Sobocka, et al. 1997; Sobocka; Sobocka, et al. 2000; Babinska, et al.). JAM was localized at intercellular junctions of mouse endothelial and epithelial cells (Martin-Padura, et al.). Similarly, the platelet antibody M.Ab.F11 was found to recognize F11R molecules present at intercellular junctions of cultured human umbilical vein endothelial cells (Sobocka, et al. XVIII ISTH *Congress, July,* 2001, Paris, France, Abs #P1902; Babinska et al., manuscript submitted, 2005). A recent study conducted by the inventors (Babinska, et al. 2002) has determined that two domains of F11R are critical for the induction of platelet aggregation by M.Ab.F11 and the adhesion of platelets to M.Ab.F11. Heretofore, the role of F11R in physiological and pathophysiological processes involving the adhesion of platelets to cytokine-inflamed endothelial cells has remained unknown. The inventors have now determined that the N-terminus of F11R and the first Ig fold of F11R contain protein sequences which are critical for the adhesion of platelets to endothelial cells, and that the recombinant soluble F11R protein and F11R-peptides block approximately 60% of the force of adhesion of platelets to cytokine-treated EC, demonstrating the involvement of the F11R protein in platelet-endothelial cell interactions, which under pathological conditions, result in thrombosis, atherosclerosis and other disorders involving thrombosis formation.

SUMMARY OF THE INVENTION

The present invention provides the full length cDNA sequence of the F11 receptor (F11R) (SEQ ID NO: 6) and the encoded F11R amino acid sequence (SEQ ID NO: 7). The present invention also provides F11R-antagonists including antibodies directed to the F11R as antagonists, peptide antagonists and peptidomimetic drugs that inhibit the biological action of the F11R protein.

The present invention further provides a therapeutic regimen or plan of treatment to inhibit platelet aggregation and adhesion, comprising administering F11R antagonist(s) separately or together with one or more additional compounds that contribute to a more favorable therapeutic outcome, e.g., treating and preventing the formation of atherosclerotic plaques, thrombosis, and the like. The regimen (i.e., a plan or course of treatment) for decreasing platelet aggregation and/or adhesion between platelets and endothelial cells in a subject in need thereof, comprises, administering to the subject an amount of an F11 receptor (F11R) antagonist(s) suitable to inhibit platelet aggregation and/or the adhesion between the endothelial cell and the platelet.

The present invention is directed to methods and compositions for treating F11R-mediated disorders such as thrombosis, atherosclerosis, plaque formation, heart attacks, inflammatory diseases of the nervous system, hypertension, stroke, angiogenesis, cancer, and all other clinical disorders involving thrombus formation, as detailed above. The invention is also directed to methods for the treatment and prevention of excessive bleeding under physiological procedures, including the prevention of excessive bleeding following wound injury. The present invention provides specific compositions containing at least one F11R-antagonist peptide which inhibits, suppresses or causes the cessation of at least one F11R-mediated biological activity in a mammal, and preferably humans. Another embodiment of the present invention is the preparation of peptidomimetic drugs that have a structure that mimics the active site of F11R and thus inhibit its biological action. An example of the relationship of the structure of such a drug to the structure of the F11R protein is the relationship between the structure of morphine and the protein beta-endorphin.

Nucleic acid molecules coding for any of the above F11R-antagonist proteins, fragments and peptides of the present invention, expression vectors which include any of such nucleic acid molecules, as well as related host cells containing such nucleotide sequences or vectors, are also contemplated by the present invention.

Still another embodiment of the present invention is directed to antibodies raised against the F11R-antagonist proteins, F11R antibody fragments, peptidomimetics and peptides of the present invention.

In accordance with the present invention, the F11R antagonists encompass compounds that mimic F11R, which when present in sufficient amounts will occupy one or more relevant molecular and/or cellular F11R binding sites that normally would be occupied by F11R in its role as a mediator of platelet aggregation and adhesion. These compounds include small molecule organic compounds, peptides, peptidomimetics, or polypeptides, that structurally resemble a portion of F11R and compete for F11R binding sites on homophilic or heterophilic F11R binding partners.

F11R antagonists also encompass compounds, peptides and polypeptides that bind directly to F11R thereby impairing its aggregative/adhesive function. This group encompasses small molecule organic compounds, ligands, polypeptides, antibodies or antibody fragments, recombinant engineered proteins and antibodies that specifically bind to a region on F11R thereby inhibiting its participation in platelet aggregation and adhesion.

In an even additional embodiment of the invention, the peptide or polypeptide may comprise the extracellular domain of F11R or an aggregation/adhesion inhibiting portion thereof. Non-limiting examples of such portions of the F11R extracellular domain are exemplified by SEQ ID NO: 1 or SEQ ID NO: 4. In general, more than one antagonist may be administered. This may be especially desirable when the administered antagonists have distinct modes of inhibition, such as: (a) one antagonist is from Group A and one is from Group B; (b) each of the administered antagonists is from Group A, but each mimics distinct portions of the F11R, and (c) each of the administered antagonists is from Group B, but each of the antagonist binds to a distinct portion of the F11R, thereby inhibiting the aggregating/adhesion functions of the respective portions of F11R.

With respect to embodiments encompassing antibody antagonists, the antibody or functional fragment thereof can be a chimeric antibody, a humanized antibody or an autoantibody. Non-limiting examples of such antibodies comprise M.Ab.F11, the Fab, Fab', or F(ab')$_2$.

Preferably, the antibodies of the present invention are raised against those F11R sequences and F11R-antagonist peptides whose sequences coincide with the corresponding sequences of a mammalian F11R or Junctional Adhesion Molecule (JAM) proteins. The antibodies of the present invention can recognize, antagonize or neutralize the activity of F11R. Both polyclonal antibodies and monoclonal antibodies of various chimeric combinations are contemplated by the present invention. Examples of such antibodies include M.Ab.F11.

An additional embodiment of the present invention encompasses a method of inhibiting platelet aggregation or platelet adhesion to an endothelial cell in a subject in need thereof, comprising:

administering an antagonist of F11R that either binds to the extracellular portion of F11R, or mimics the extracellular domain of F11R or portions thereof, in an amount sufficient to inhibit platelet aggregation or platelet adhesion to endothelial cells. In accordance with the present invention, the F11R antagonist comprises a compound, a peptide, a peptidomimetic, or an antibody or functional fragment thereof that inhibits F11R-mediated aggregation and adhesion. The antibody or functional fragment thereof can be a chimeric or fully humanized antibody or an autoantibody. Further, the peptide can comprise the extracellular domain of F11R or an aggregation/adhesion-inhibiting portion or fragment thereof.

The present invention also provides a compound including a peptidomimetic which interacts sterically with the binding site of a F11R molecule, the peptidomimetic including a peptidomimetic having the SEQ ID NO: 4D. The present invention further provides a method for treating a disorder comprising administering peptide 4D to a mammal.

These and other embodiments of the invention will be readily apparent to those of ordinary skill in view of the disclosure herein.

BRIEF DESCRIPTION OF THE FIGURES

FIG. 2D demonstrates that Peptide 1 SEQ ID NO: 1 completely inhibited platelet aggregation (see the flat tracing, "plus Peptide 1"). Similarly, experiments were carried-out (see FIG. 2C) in which the F11R-peptide of SEQ ID NO: 4 was preincubated with platelets for about 42 sec prior to the addition of M.Ab.F11 (0.3 μg/ml) followed by addition of ADP (0.5 μM).

FIG. 5A shows that Fab fragments of antibody M.Ab.F11 blocked 20% of the adhesion of non-activated platelets to the aortic cells, whereas FIG. 5B demonstrates that the Fab fragments were effective in blocking over 90% of the adhesion of collagen-activated platelets to the endothelial cell monolayers.

As shown in FIG. 6A, a 60% inhibition of the adhesion of non-activated platelets to the cytokine-treated HAEC monolayers could be achieved in the presence of 100 μg Fab (BAR 2), and 80% inhibition of adhesion occurred in the presence of 200 μg/ml Fab (BAR 3). Similarly, as shown in FIG. 6B, a 70% inhibition of the adhesion of collagen-activated platelets to the endothelial cells could be achieved in the presence of 100 μg Fab (BAR 2), whereas a stronger inhibition (95% inhibition) of the platelet adhesion to HAEC could be achieved in the presence of 200 μg Fab (BAR 3). (Values obtained in control experiments, "no Fab added", were set at 100%).

DETAILED DESCRIPTION OF THE INVENTION

Figures 1A, 1B:
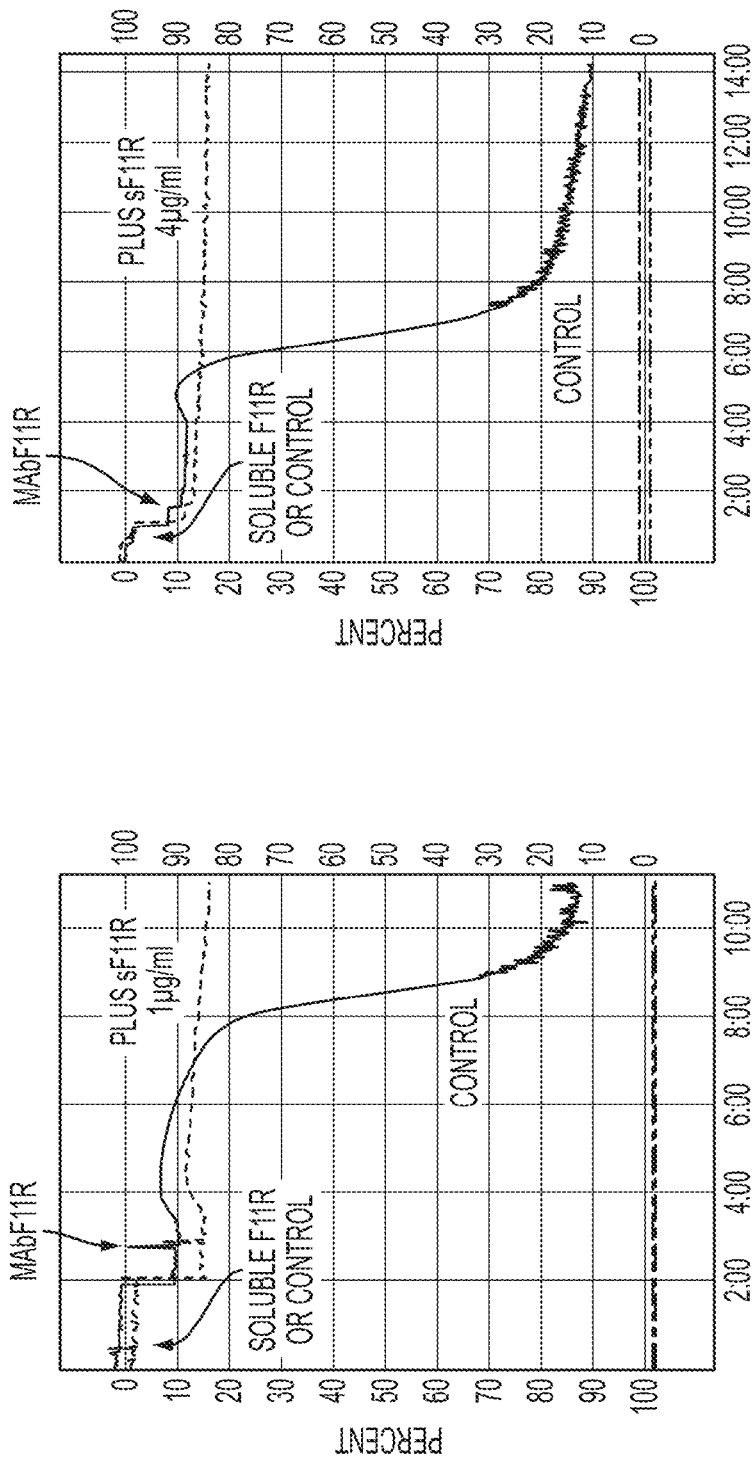
FIG. 1 demonstrates that adding a suitable amount of purified soluble extracellular portion of F11R ("sF11R") to platelet suspensions inhibits platelet aggregation in a concentration-dependent manner. Inhibition of M.Ab.F11 (M.Ab.F11R; 2.45 μg/ml)-induced platelet aggregation by the addition of sF11R (soluble F11R) was observed at two concentrations of sF11R, 1 μg/ml (1A) and 4 μg/ml (1B), with complete, irreversible platelet aggregation observed at 4 μg/ml sF11R (1B). Control tracing show the full-blown platelet aggregation that occurred in the absence of sF11R. These results indicate that sF11R, and therefore native F11R as well, comprise at least one peptide sequence that is sufficient to inhibit M.Ab.F11-induced platelet aggregation.

The present invention is directed to F11R-antagonists and particularly antibody directed against F11R, the Fab, Fab', F(ab')$_2$ fragments of such antibody, as well as single-chain anti-F11R antibodies. By "F11R-antagonist" is meant molecules that inhibit, suppress or cause the cessation of at least one F11R-mediated biological activity by, e.g., interfering with, blocking or otherwise preventing or regulating the interaction or binding of F11R to its target, e.g. F11R on another cell, or another protein that F11R binds to such as itself or other JAMs, to the leukocyte function associated antigen-1 (LFA-1) (Ostermann et al., 2002, Nat. Immunol. 3, 151-158), the integrins GPIIb/IIIa and $\alpha_v\beta_3$, as well as other binding proteins.

In accordance with the present invention, novel F11R-antagonist peptides derived from or corresponding to the F11R have been isolated and synthesized. These peptides possess F11R antagonistic properties including the ability to selectively bind to F11R and inhibit F11R-mediated biological activity which, for example, is associated with adhesion of platelets to endothelial cells in mammals. The peptides of the present invention preferably correspond to specific portions of the native human F11 receptor and include variations thereof, and therefore are non-immunogenic when administered to humans. The peptides of the present invention can effectively block collagen-induced platelet aggregation and secretion and thereby are efficacious in regard to, inter alia, the prevention of excessive bleeding following an injury, under physiological conditions. Moreover, under pathological conditions, the uncontrolled accumulation of platelets in the vasculature, on the luminal surface of the inflamed endothelium or at exposed collagen sites within the injured vasculature results in excessive platelet aggregation, plaque and thrombus formation, atherosclerosis and stroke. In the context of the invention, the term "subject in need thereof" can be an animal, mammal or human that is at risk for, or is already experiencing symptoms of the foregoing conditions. The collagen-induced platelet aggregation blocking ability of the F11R-antagonist peptides of the present invention provides heretofore unrecognized treatment and prevention options in subjects in need thereof, i.e., diseases and disorders associated with excessive platelet aggregation.

The F11R-antagonist peptides of the present invention substantially correspond to the amino acids of the N-terminus or first Ig domain of human F11R.

A preferred F11R-antagonist peptide of the present invention is a sequence of the N-terminal peptide of the F11R structure: SVTVHSSEPEVRIPENNPVKLSC (SEQ ID NO: 1).

Another preferred F11R-antagonist peptide of the present invention is a sequence within the first Ig fold of the F11R structure: KSVTREDTGTYTC (SEQ ID NO: 4).

Homologs, analogs and fragments of these peptides which maintain F11R-antagonist activity in a mammal, particularly humans are also contemplated by the present invention.

Another aspect of the present invention provides methods of interfering with, blocking or otherwise preventing the interaction or binding of platelets to endothelial cells via F11R by employing the F11R-antagonists contemplated by the present invention.

The present invention also provides compositions for the treatment of F11R-mediated disorders such as thrombosis, inflammatory thrombosis, atherosclerosis, atherosclerotic plaque formation, angiogenesis, heart attacks, hypertension, stroke and all other clinical disorders involving thrombus formation, in animals, including humans and includes methods of treating such disorders. The present invention is also directed to the treatment and prevention of excessive bleeding following a wound injury and inflammatory diseases of the nervous system. The compositions include at least one of the F11R-antagonists, preferably at least one F11R peptide antagonist according to the present invention, admixed with a pharmaceutically acceptable carrier.

In accordance with the present invention, the protein F11R serves a significant role in the adhesion of platelets to inflamed endothelial cells. The present invention has identified that the activity of F11R is critical for initiating platelet adherence to the vasculature with the formation of atherosclerotic plaques in blood vessels and for the formation of thrombi. Thus, any agents, chemicals or drugs that inhibit the action of F11R (named here collectively: F11R-antagonists) will serve as powerful inhibitors of thrombus development in the circulation. Accordingly, the present invention provides F11R-antagonists as drugs useful for the prevention and treatment of thrombosis, atherosclerosis, plaque formation, heart attacks, strokes, hypertension, immunothrombocytopenia, posttransfusion purpura, acute and chronic immunothrombocytopenia, acquired disorders of platelet function, myeloproliferative disorders, uremia, liver disease, cardiopulmonary bypass, various types of thrombosis, inflammatory thrombosis, peripheral vein thrombosis, coronary artery thrombosis and other arterial thrombosis, atherosclerosis, disorders of angiogenesis, cancer growth and metastasis, and all other human disorders that involve angiogenesis and/or thrombus formation.

Platelet "aggregation" refers to any aggregative event between two or more platelets. Thus, the term "platelet aggregation" encompasses platelets aggregating with other platelets. The adherence or binding of platelets to something other than platelets is generally referred to by the term "adhesion" or "binding." Platelet adhesion may therefore refer to platelet binding to collagen, basement membranes, cells expressing functional F11R on its cell surface either normally or due to pathological inflammatory disease states, or by gene transfer technology. For example, inflamed endothelial cells, which express an unmodified/wild type F11R or variants of the F11R polypeptide, may participate in platelet adhesion. Adhesion of platelets may also be observed by determining the F11R-mediated adhesion or binding of a platelet to an artificial substrate or matrix comprising F11R or variants thereof, as well as a platelet binding factor, protein, polypeptide, such as e.g., the extracellular domain of F11R, or an immobilized antibody directed to a platelet cell surface protein. The substrate may be virtually any substrate used in binding assays, a preparation of cell membranes comprising F11R, or a monolayer of fixed F11R-expressing cells.

The term "proinflammatory" or "inflammation-inducing" refers to the tendency of an experimental or physiological stimulus to induce the EC layer of the endothelium to undergo biochemical or morphological changes similar to those observed in actual pathological states or medical conditions. One non-limiting example of such a stimulus is the effect resulting from contacting ECs with particular cytokines under suitable conditions. In such cases, the ECs acquire one or more characteristics of an inflammatory state or an inflammatory condition. One relevant effect of contacting ECs with one or more proinflammatory cytokines is that the cellular localization of F11R on the EC surface is altered. Specifically, the pattern of F11R changes from its normal or non-inflammatory state, characterized by F11R being concentrated at the junctional regions, i.e., regions of cell-cell contact between ECs, to a more uniform distribution along the EC cell surface.

Terms used to describe diminished platelet aggregation and adhesion such as "decreased," "inhibited," "impaired," and the like, refer to lowered levels of platelet aggregation or platelet adhesion without requiring any specific level of diminution, such as a complete or 100% inhibition.

One aspect of the invention is directed to methods of identifying a compound which prevents the adhesion of platelets to endothelial cells and that inhibits platelet aggregation, also referred to as "F11R-antagonists."

The term "compound" is taken to include both organic compounds such as peptides, as well as inorganic compounds such as ion chelators or opiates. Antibodies, e.g., polyclonal or monoclonal antibodies directed against F11R, the Fab, Fab', F(ab')$_2$ fragments of such antibodies, as well as single-chain anti-F11R antibodies can also be considered as compounds useful in the present methods.

When applicable, an anti-F11R antibody (e.g., M.Ab.F11) or antigen-binding fragment thereof is a humanized antibody. A "humanized antibody" is an antibody in which protein engineering is used to reduce the amount of 'foreign' protein sequence by substituting host antibody (e.g., mouse, rat) constant regions and the variable-domain framework regions with sequences that are found in human antibodies. It is further contemplated that when complete antibody molecules are to be employed, they may also be humanized or chimeric antibodies. Generally, a "chimeric antibody" is one where the constant regions of host origin, e.g., mouse or rat, are replaced by those of a human antibody.

Other preferred compounds include chemical compounds that can be derived from the knowledge of the sequence of the F11R, from each of the above sequences (i.e. SEQ ID NOS: 1-7) and from the combination of the sequences together. These include linear sequences, cyclic sequences, annealing of the peptides together (preferably SEQ ID NOS: 1 and 4), and any other possible derivations using standard peptide chemistry techniques. In one embodiment the present invention contemplates any compound whose structure is based on the interaction of peptides 1 and 4 (SEQ ID NOS: 1 and 4), which form the binding site of the mature human platelet F11R.

As used herein a "mimetic" or "peptidomimetic" of a compound's functional site refers to a compound in which chemical structures of protein or peptide sequences necessary for functional activity of a compound's functional site have been replaced with other chemical structures that mimic the conformation of the functional site. An example of a peptidomimetic contemplated by the present invention includes a compound (e.g. a small organic molecule) including portions with residues which interact sterically with the binding site of the F11R molecule. In accordance with the present invention, F11R peptidomimetic drugs can be designed on the basis of, for example, peptides having SEQ ID NOs. 1 and 4 and the tertiary structure of the binding site of F11R, including parts of the protein containing these sequences. Such peptidomimetic drugs with structural relationships analogous to that observed between morphine, enkephalins and beta-endorphins, are suitable as therapeutic agents. The design and synthesis of peptidomimetic molecules continues to be at the forefront of drug design and discovery and many peptidomimetic frameworks and methods for their synthesis have been developed (Babine, R. E.; Bender, S. L., *Chem. Rev.*, 97:1359, 1997; Hanessian, S.; et al., *Tetrahedron*, 53:12789, 1997; Fletcher, M. D.; Cambell, M. C., *Chem. Rev.*, 98:763, 1998), these teachings are incorporated herein by reference.

The peptidomimetics in accordance with the present invention can be developed, for example, with the aid of computerized molecular modeling. In a preferred embodiment, the present invention provides a pharmaceutical composition comprising SEQ ID NO: 1 or SEQ ID NO: 4 wherein SEQ ID NO: 1 or SEQ ID NO: 4 comprises peptidomimetics that are capable of specific binding with the F11R binding site. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biochemical property or pharmacological activity), such as SEQ ID NO: 1 or SEQ ID NO: 4, but have one or more peptide linkages optionally replaced by a linkage selected from the group consisting of: —CH$_2$NH—, —CH$_2$S—, —CH$_2$CH$_2$—, —CH=CH— (cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., *Vega Data* (March 1983), Vol. 1, Issue 3, "Peptide Backbone Modifications" (general review); Morley, J. S., *Trends Pharm Sci* (1980) pp. 463-468 (general review); Hudson, D. et al., (1979) *Int J Pept Prot Re* 14:177-185 (—CH$_2$NH—, —CH$_2$—CH$_2$—); Spatola, A. F. et al., (1986) *Life Sci* 38:1243-1249 (—CH$_2$S); Hann, M. M., (1982) *J Chem Soc Perkin Trans* 1307-314 (—CH=CH—, cis and trans); Almquist, R. G. et al., (1980) *J Med Chem* 23: 1392-1398 (—COCH$_2$—); Jennings-White, C. et al., (1982) *Tetrahedron Lett* 23:2533 (—COCH$_2$—); Szelke, M. et al., European Appln. EP 45665 (1982) CA: 97:39405 (1982) (—CH(OH)CH$_2$—); Holladay, M. W. et al., (1983) *Tetrahedron Lett* 24:4401-4404 (—C(OH)CH$_2$—); and Hruby, V. J., (1982) *Life Sci* 31:189-199 (—CH$_2$S—); each of which is incorporated herein by reference.

In another embodiment, a particularly preferred non-peptide linkage is —CH$_2$NH—. Such peptidomimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

A variety of designs for peptidomimetics are possible. For example, cyclic peptides, in which the necessary conformation for binding is stabilized by nonpeptides, are specifically contemplated. U.S. Pat. No. 5,192,746 to Lobl, et al., U.S. Pat. No. 5,169,862 to Burke, Jr., et al, U.S. Pat. No.

5,539,085 to Bischoff, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference, describe multiple methods for creating such compounds. Synthesis of nonpeptide compounds that mimic peptide sequences is also known in the art. Eldred, et al., (*J. Med. Chem.* 37:3882 (1994)) describe nonpeptide antagonists that mimic the peptide sequence. Likewise, Ku, et al., (*J. Med. Chem.* 38:9 (1995)) give further elucidation of the synthesis of a series of such compounds. Derivatives of e.g. SEQ. ID. NO.: 1 or SEQ ID NO: 4 can be produced using recombinant nucleic acid molecule techniques.

Modifications to a specific peptide may be deliberate, as through site-directed mutagenesis and amino acid substitution during biosynthesis, or may be accidental such as through mutations in hosts, which produce the peptide. Peptides including derivatives can be obtained using standard mutagenesis techniques such as those described in Sambrook et al., Molecular Cloning, Cold Spring Harbor Laboratory Press (1989). For example, Chapter 15 of Sambrook describes procedures for site-directed mutagenesis of cloned DNA. Derivatives of SEQ ID NOs.: 1 and 4 include, but are not limited by modification occurring during or after translation, for example, by phosphorylation, glycosylation, crosslinking, acylation, proteolytic cleavage, linkage to a therapeutic protein, an antibody molecule, membrane molecule or other ligand (see Ferguson et al., 1988, *Annu. Rev. Biochem.* 57:285-320). Specific types of genetically produced derivatives also include, but not limited by amino acid alterations such as deletions, substitutions, additions, and amino acid modifications. A "deletion" refers to the absence of one or more amino acid residue(s) in the related peptide. An "addition" refers to the presence of one or more amino acid residue(s) in the related peptide. Additions and deletions to a peptide may be at the amino terminus, the carboxy terminus, and/or internal, can be produced by mutation in e.g., SEQ ID NO: 1 encoding DNA and/or by peptide post-translation modification. Amino acid "modification" refers to the alteration of a naturally occurring amino acid to produce a non-naturally occurring amino acid. Analogs of e.g. SEQ ID NO: 1 with unnatural amino acids can be created by site-specific incorporation of unnatural amino acids into polypeptides during the biosynthesis, as described in Christopher J. Noren, Spencer J. Anthony-Cahill, Michael C. Griffith, Peter G. Schultz, 1989 *Science,* 244: 182-188. A "substitution" refers to the replacement of one or more amino acid residue(s) by another amino acid residue(s) in the peptide. Mutations can be made in e.g., SEQ ID NO: 1 encoding DNA such that a particular codon is changed to a codon, which codes for a different amino acid. Such a mutation is generally made by making the fewest nucleotide changes possible. A substitution mutation of this sort can be made to change an amino acid in the resulting peptide in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting peptide. To some extent the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids. Although proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp). Derivatives can contain different combinations of alterations including more than one alteration and different types of alterations.

The ability of the derivative to retain some activity can be measured using techniques described herein and/or using techniques known to those skilled in the art for measuring the F11R receptor binding activity. "Derivatives" of e.g., SEQ. ID. NO.: 1 are functional equivalents having similar amino acid sequence and retaining, to some extent, the activities of SEQ ID NO: 1. By "functional equivalent" is meant the derivative has an activity that can be substituted for the activity of SEQ. ID NO:1. Preferred functional equivalents retain the full level of F11R-binding activity as measured by assays known to these skilled in the art. Preferred functional equivalents have activities that are within 1% to 10,000% of the activity of e.g., SEQ ID NO: 1, more preferably between 10% to 1000%, and more preferably within 50% to 200%. Derivatives have at least 50% sequence similarity, preferably 70%, more preferably 90%, and even more preferably 95% sequence similarity to SEQ. ID. NO: 1. "Sequence similarity" refers to "homology" observed between amino acid sequences in two different polypeptides, irrespective of polypeptide origin. A "residue" refers to an amino acid incorporated in the peptide by an amide bond, for example. Approaches to designing peptide mimetics are known in the art. For example, see Farmer, P. S. in *Drug Design* (E. J. Ariens, ed). Academic Press, New York, 1980, vol. 10, pp. 119-143; Ball J. B. and Alewood, P. F. (1990) *J. Mol. Recognition.* 3:55, Morgan B. A. and Ganor, J. A. (1985) *Ann. Rev. Med. Chem.* 24:243 and Freidinger R. M. (1989) *Trends Pharmacol. Sci:* 10:270, incorporated herein by reference. In one embodiment, the present invention contemplates all peptidomimetics which can be designed based on the knowledge of the sequence and of the three-dimensional structure of the F11R molecule of the invention including but not limited to all mimetic compounds which can be conventionally synthesized by an ordinarily skilled chemist to bind to, antagonize, act as an agonist, inhibit, promote, block, or otherwise functionally interact with the binding site of the F11R.

Most preferred compounds of the present methods are peptides which are made to resemble the monoclonal antibody F11 ("M.Ab.F11") binding site on platelets.

In one example a peptidomimetic entitled 4D may be used. Peptidomimetic 4D is based on the amino acid sequence of the peptide of SEQ ID NO: 4. SEQ ID NO: 4 is a 13 amino acid sequence located within the first immunoglobulin fold of the F11R protein. A 13-mer peptide with this sequence is an inhibitor of the biological activities of F11R measured both in vitro and in cell cultures. A nonnatural peptide that mimics the structure of the peptide of SEQ ID NO: 4 can be synthesized with substituted D-amino acids in the two main sites for cleavage by endopeptidases trypsin and with the carboxyl group amidated ($CONH_2$) for the prevention of dimeric-disulphides. This modification resulted in the design of a mimetic-peptide referred to herein as peptide 4D. The sequence of F11R peptide 4D is dKSVT dREDTGTYTC-$CONH_2$ (SEQ ID NO: 10), with the underlined letters indicating the positions of the two substituted D-amino acids. Use of peptide 4D is further described in Example 9 below.

Other peptidomimetics can also be used. In another example based on SEQ ID NO: 4, the sequence of other F11R peptides can be, among others, KSVT dREDTGTYTC-$CONH_2$ (SEQ ID NO: 11), SVT dREDTGTYTC-$CONH_2$ (SEQ ID NO: 12), VT dREDTGTYTC-$CONH_2$ (SEQ ID NO: 13), T dREDTGTYTC-$CONH_2$ (SEQ ID NO: 14), dREDTGTYTC-$CONH_2$ (SEQ ID NO: 15), REDTGTYTC-$CONH_2$ (SEQ ID NO: 16), EDTGTYTC-$CONH_2$ (SEQ ID NO: 17), DTGTYTC-$CONH_2$ (SEQ ID NO: 18), TGTYTC-$CONH_2$ (SEQ ID NO: 19) or GTYTC-$CONH_2$ (SEQ ID NO: 20). In other examples, the sequence of other F11R peptides can be, among others, dKSVTdREDTGTYTC (SEQ ID NO: 21), dKSVTdREDTGTYT (SEQ ID NO: 22), dKSVT dREDTGTY (SEQ ID NO: 23), dKSVTdREDTGT (SEQ ID NO: 24), dKSVTdREDTG (SEQ ID NO: 25), dKSVT dREDT (SEQ ID NO: 26), dKSVTdRED (SEQ ID NO: 27), dKSVTdRE (SEQ ID NO: 28), dKSVTdR (SEQ ID NO: 29), dKSVTd (SEQ ID NO: 30) or dKSVT (SEQ ID NO: 31).

In another example, a peptidomimetic entitled 1P may be used. Peptidomimetic 1P is based on the amino acid sequence of the peptide of SEQ ID NO: 1. SEQ ID NO: 1 is a 23 amino acid sequence located within the N-terminus of the F11R protein. Peptidomimetic 1P can be many variations including, but not limited to, VTVHSSEPEVRIP-ENNPVKLSC (SEQ ID NO: 32), TVHSSEPEVRIPEN-NPVKLSC (SEQ ID NO: 33), VHSSEPEVRIPEN-NPVKLSC (SEQ ID NO: 34), HSSEPEVRIPENNPVKLSC (SEQ ID NO: 35), SSEPEVRIPENNPVKLSC (SEQ ID NO: 36), SEPEVRIPENNPVKLSC (SEQ ID NO: 37), EPE-VRIPENNPVKLSC (SEQ ID NO: 38), PEVRIPEN-NPVKLSC (SEQ ID NO: 39), EVRIPENNPVKLSC (SEQ ID NO: 40), VRIPENNPVKLSC (SEQ ID NO: 41), RIP-ENNPVKLSC (SEQ ID NO: 42), IPENNPVKLSC (SEQ ID NO: 43), PENNPVKLSC (SEQ ID NO: 44), ENNPVKLSC (SEQ ID NO: 45), NNPVKLSC (SEQ ID NO: 46), NPVKLSC (SEQ ID NO: 47), PVKLSC (SEQ ID NO: 48) or VKLSC (SEQ ID NO: 49). Other variations of peptidomimetic 1P include, but are not limited to, SVTVHSSEPE-VRIPENNPVKLS (SEQ ID NO: 50), SVTVHSSEPEVRIP-ENNPVKL (SEQ ID NO: 51), SVTVHSSEPEVRIPENNPVK (SEQ ID NO: 52), SVT-VHSSEPEVRIPENNPV (SEQ ID NO: 53), SVT-VHSSEPEVRIPENNP (SEQ ID NO: 54), SVTVHSSEPE-VRIPENN (SEQ ID NO: 55), SVTVHSSEPEVRIPEN (SEQ ID NO: 56), SVTVHSSEPEVRIPE (SEQ ID NO: 57), SVTVHSSEPEVRIP (SEQ ID NO: 58), SVTVHSSEPEVRI (SEQ ID NO: 59), SVTVHSSEPEVR (SEQ ID NO: 60), SVTVHSSEPEV (SEQ ID NO: 61), SVTVHSSEPE (SEQ ID NO: 62), SVTVHSSEP (SEQ ID NO: 63), SVTVHSSE (SEQ ID NO: 64), SVTVHSSE (SEQ ID NO: 65), SVT-VHSS (SEQ ID NO: 66), SVTVHS (SEQ ID NO: 66) and SVTVH (SEQ ID NO: 67).

"F11R" refers to a receptor protein on the surface of human platelets as a target for a stimulatory M.Ab.F11. "F11R" is also referred to as human ortholog of the murine protein called junctional adhesion molecule (JAM), specifically named JAM-1 and JAM-A. F11R from either platelets or endothelial cells comprises an extracellular domain consisting of two Ig-folds, a transmembrane domain and a short cytoplasmic portion. The cDNA encoding the F11R can be engineered, e.g., to delete the transmembrane and cytoplasmic domain thereby providing a polynucleotide encoding the extracellular domain. Expression of the F11R extracellular domain in eukaryotic cells results in its synthesis and secretion, thereby indicating that it is a soluble polypeptide.

"F11R antagonists" and "F11R antagonist peptides" further refers to any compound that can bind to the active site of the F11R protein, specifically, but not limited to a pocket formed by the N-terminal 23 amino acid region and 13 amino acid region in the first Ig fold. By such binding, the action of F11R is inhibited, i.e. alignment of platelets and endothelial cells in F11R-mediated trans-homophilic interaction through the steric pocket, as depicted in FIG. 1, is blocked so that platelet aggregation or thrombosis, atherosclerosis, heart attacks, strokes, and all other human disorders that involve thrombus formation, can be prevented or treated. By "F11R antagonist peptide" is also meant a peptide that inhibits, suppresses or causes the cessation of at least one F11R mediated biological activity by e.g. interfering with or otherwise preventing the interaction or binding of platelets to endothelial cells and thereby inhibit platelet aggregation or interfering with the role of some protein in angiogenesis and thus preventing the growth of tumors.

In accordance with the present invention, two peptide sequences of the F11R have been determined the sequences correspond to (the N-terminus SVTVHSSEPEVRIPEN-NPVKLSC (SEQ ID NO: 1), and the first Ig fold sequence KSVTREDTGTYTC (SEQ ID NO: 4). The peptide sequences of the present invention inhibit the adhesion of platelets to endothelial cells and inhibit platelet aggregation.

As used herein, "peptide" refers to a linear series of amino acid residues linked to one another by peptide bonds between the alpha-amino and carboxy groups of adjacent amino acid residues. The term "synthetic peptide" is intended to refer to a chemically derived chain of amino acid residues linked together by peptide bonds. The term "synthetic peptide" is also intended to refer to recombinantly produced peptides in accordance with the present invention. According to the present invention, preferred F11R antagonists include peptides (referred to herein as "F11R antagonist peptides") and antibodies. Additionally, analogs, homologs and fragments of the novel peptides provided herein are included within the scope of the term "F11R antagonist peptide".

By "homologs" is meant the corresponding peptides from F11R proteins of other mammalian species substantially homologous at the overall protein (i.e., mature protein) level to human F11R, so long as such homologous peptides retain the F11R antagonist activity.

By "analogs" or "F11R-Antagonist Peptide Analysis" is meant peptides which differ by one or more amino acid alterations, which alterations, e.g., substitutions, additions or deletions of amino acid residues, do not abolish the F11R antagonist properties of the relevant peptides. Thus, an analog can comprise a peptide having a substantially identical amino acid sequence to a peptide provided herein and in which one or more amino acid residues have been conservatively or non-conservatively substituted. Examples of conservative substitutions include the substitution of a non-polar (hydrophobic) residue such as isoleucine, valine, leucine or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated. Examples of non-conservative substitutions include the substitution of a non-polar (hydrophobic) residue such as isoleucine, valine, leucine, alanine, methionine for a polar (hydrophilic) residues such as cyteine, glutamine, glutamic acid, lysine and/or a polar residue for a non-polar residue.

The phrase "conservative substitution" also includes the use of chemically derivatized residues in place of a non-derivatized residues as long as the peptide retains the requisite F11R antagonist, inhibition properties as conventionally measured. Analogs also include the presence of additional amino acids or the deletion of one or more amino acids which do not affect F11R-mediated biological activity. For example, analogs of the subject peptides can contain an N- or C-terminal cysteine, by which, if desired, the peptide can be covalently attached to a carrier protein, e.g., albumin. Such attachment, it is believed, will minimize clearing of the peptide from the blood and also prevent proteolysis of the peptides. In addition, for purposes of the present invention, peptides containing D-amino acids in place of L-amino acids are also included in the term "conservative substitution". The presence of such D-isomers can help minimize proteolytic activity and clearing of the peptide.

The term "fragment" refers to any subject peptide having an amino acid sequence shorter than that of any peptide depicted in SEQ ID NOS: 1-5 and 7 and which fragment retains the F11R-mediated antagonist activity of the subject peptides.

The practice of the present invention employs, unless otherwise indicated, conventional techniques of synthetic organic chemistry, protein chemistry, molecular biology, microbiology, and recombinant DNA technology, which are well within the skill of the art. These techniques are applied in connection with peptide synthesis, recombinant production of peptides and peptide mutagenesis, for example. Such techniques are explained fully in the literature. See e.g., Scopes, R. K., *Protein Purification Principles and Practices*, 2d ed. (Springer-Verlag. 1987), *Methods in Enzymology* (M. Deutscher, ed., Academic Press, Inc. 1990), Sambrook, et al., *Molecular Cloning: A laboratory Manual*, 2d ed., (Cold Spring Harbor Press, Cold Spring Harbor, N.Y., 1989), *Handbook of Experimental Immunology*, Vols. I-IV (D. M. Weir and C. C. Blackwell, eds., 1986, Blackwell Scientific Publications), House, *Modern Synthetic Reactions*, 2d ed., (Benjamin/Cummings, Menlo Park, Cal., 1972).

The peptides of the present invention, homologs, analogs and fragments thereof can be synthesized by a number of known techniques. For example, the peptides may be prepared using the solid-phase synthetic technique initially described by Merrifield, in J. Am. Chem. Soc. 85:2149-2154 (1963). Other peptide synthesis techniques can be found in M. Bodanszky, et al. *Peptide Synthesis*, John Wiley & Sons, 2d Ed., (1976) and other references readily available to those skilled in the art. A summary of polypeptide synthesis techniques can be found in J. Stuart and J. D. Young, *Solid Phase Peptide Synthesis*, Pierce Chemical Company, Rockford, Ill., (1984). Peptides may also be synthesized by solution methods as described in *The Proteins*, Vol. II. 3d Ed., Neurath, H. et al., Eds., p. 105-237, Academic Press, New York, N.Y. (1976). Appropriate protective groups for use in different peptide syntheses are described in the above-mentioned texts as well as in J. F. W. McOmie, *Protective Groups in Organic Chemistry*, Plenum Press, New York, N.Y. (1973). The peptides of the present invention can also be prepared by chemical or enzymatic cleavage from larger portions of the F11R molecule or from the entire F11R molecule.

Additionally, the peptides of the present invention can also be prepared by recombinant DNA techniques (see e.g. *Current Protocols in Molecular Cloning* Ausubel et al., 1995, John Wiley & Sons, New York); Sambrook et al., 1989, *Molecular Cloning: A Laboratory Manual*, Second Edition, Cold Spring Harbor Laboratory Press, New York; Coligan et al. *Current Protocols in Immunology*, John Wiley & Sons Inc., New York, N.Y. (1994)). The skilled artisan understands that any of a wide variety of expression systems can be used to provide the recombinant peptides of the present invention. The precise host cell used is not critical to the invention. The F11R antagonist peptides can be produced in a prokaryotic host (e.g. *E. coli*), or in a eukaryotic host (e.g., *S. cerevisiae* or mammalian cells, e.g. COS 1, CHO, NIH3T3, and JEG3 cells, or in the cells of an arthropod, e.g. *S. frugiperda*). Such cells are available from e.g. the American Type Culture Collection, Manassas, Va. The method of transfection and the choice of expression vehicle will depend on the host system selected. Transformation and transfection methods are described, e.g. in Sambrook et al. supra; expression vehicles can be chosen from those provided e.g. in *Cloning Vectors: A Laboratory Manual* P. H. Powels et al (1985), Supp. 1987.

For most of the amino acids used to build proteins, more than one coding nucleotide triplet (codon) can code for a particular amino acid residue. This property of the genetic code is known as redundancy. Therefore, a number of different nucleotide sequences can code for a particular subject F11R antagonist peptide. The present invention also contemplates a deoxyribonucleic acid (DNA) molecule or segment that defines a gene coding for, i.e., capable of expressing, a subject peptide or a subject chimeric peptide from which a peptide of the present invention can be enzymatically or chemically cleaved.

DNA molecules that encode peptides of the present invention can be synthesized by chemical techniques, for example, the phosphotriester method of Matteuccie, et al., *J. Am. Chem. Soc.* 103:3185 (1981). Using a chemical DNA synthesis technique, desired modifications in the peptide sequence can be made by making substitutions for bases which code for the native amino acid sequence. Ribonucleic acid equivalents of the above described DNA molecules may also be used.

A nucleic acid molecule comprising a vector capable of replication and expression of a DNA molecule defining coding sequence for a subject polypeptide or subject chimeric polypeptide is also contemplated.

The peptides of the present invention are chemically synthesized by conventional techniques such as the Merrifield solid phase technique. In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

A preferred method of solid phase synthesis entails attaching the protected or derivatized amino acid to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide. The lyophilized oligopeptides are resuspended in double distilled $H_2O$ at 2 mg/ml as stock solutions and subsequently diluted in M199-HPS for experiments. Consistent with the observed properties of the peptides of the invention, the present peptides can be used to inhibit, suppress, or cause the cessation of at least one F11R-mediated biological activity. F11R functions in the biochemical events associated with platelets aggregation and adhesion of platelets to endothelial cells. Accordingly, the present invention contemplates methods to block, interrupt or otherwise prevent the association of platelets to endothelial cells and thereby effectively treat or prevent F11R-cell associated disorders such as thrombosis, for example.

F11R-mediated disorders such as, for example, thrombosis, atherosclerosis, heart attacks and strokes are F11R-dependent therefore treatable with the F11R antagonists, preferably F11R antagonist peptides or peptidomimetics of the present invention. Other F11R related diseases are also contemplated by the present invention.

In another embodiment of the present invention, one or more F11R antagonists, e.g., F11R antagonist peptides, peptidomimetics or antibodies, are included in pharmaceutical compositions.

Preferably, compositions containing the F11R antagonist peptides or peptidomimetics of the present invention are administered intravenously to inhibit, suppress, or cause the cessation of at least one F11R-mediated biological activity. When administered intravenously, the peptide compositions can be combined with other ingredients, such as carriers and/or adjuvants. The peptides may also be covalently attached to a protein carrier, such as albumin, so as to minimize clearing of the peptides. There are no limitations on the nature of the other ingredients, except that such ingredients must be pharmaceutically acceptable, efficacious for their intended administration and cannot degrade the activity of the active ingredients of the compositions. Examples of other anti-inflammatory ingredients contemplated by the present invention include, but are not limited to anti-F11R antibodies, NSAIDS, steroids, or cyclosporin-A. When employed together with F11R antagonists, these agents may be employed in lesser dosages than when used alone.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutano, phenol, sorbic acid or thimerosal. Further, isotonic agents such as sugars or sodium chloride can be incorporated in the subject compositions.

Production of sterile injectable solutions containing the subject peptides is accomplished by incorporated these compounds in the required amount in the appropriate solvent with various ingredients enumerated above, as required, followed by sterilization, preferably filter sterilization. To obtain a sterile powder, the above solutions are vacuum-dried or freeze-dried as necessary. Further to administration by injection intravenously, peptides may also be administered parenterally intramuscularly, intraperitoneally, intrathecally, in a suppository, transdermally, topically, or orally.

When the peptides or peptidomimetics of the invention are administered orally, the pharmaceutical compositions thereof containing an effective dose of the peptide can also contain an inert diluent, as assimilable edible carrier and the like, be in hard or soft shell gelatin capsules, be compressed into tablets, or can be in an elixir, suspension, syrup or the like.

The subject peptides or peptidomimetics are thus compounded for convenient and effective administration in pharmaceutically effective amounts with a suitable pharmaceutically acceptable carrier in a therapeutically effective dose.

The peptides and peptidomimetics should preferably be administered in an amount of at least about 50 mg per dose, more preferably in an amount up to about 500 mg to about 1 gram per dose. Since the peptide compositions of this invention will eventually be cleared from the bloodstream, re-administration of the compositions is indicated and preferred.

The peptides and peptidomimetics can be administered in a manner compatible with the dosage formulation and in such amount as well be therapeutically effective. Systemic dosages depend on the age, weight and conditions of the patient and on the administration route. For example, a suitable dose for the administration to adult humans ranges from about 1 mg/kg of body weight about 10 mg per kilogram of body weight. The present invention also contemplates that the peptide or peptidomimetic compositions can be suitably coated on stents, lines, and tubes with a therapeutically effective amount of the peptide which amount can be readily determined by the skilled practitioner.

As used herein, a pharmaceutically acceptable carrier includes any and all solvents, dispersion media, coatings, antibacterial and antifungal agents, isotonic agents the like. The use of such media and agents are well-known in the art. The pharmaceutically acceptable carriers used in conjunction with the peptides of the present invention vary according to the mode of administration. For example, the compositions can be formulated in any suitable carrier for oral liquid formulation such as suspensions, elixirs and solutions. Compositions for liquid oral dosage include any of the usual pharmaceutical media such as, for example, water, oils, alcohols, flavoring agents, preservatives, coloring agents and the like. In the case of oral solid preparations (capsules and tablets) carriers such as starches, sugars, diluents, granulating agents, lubricants, binders, disintegrating agents and the like can be used. In addition, carriers such as liposomes and microemulsions can be used.

In a further aspect of the present invention, the pharmaceutical compositions of the present invention are employed for the treatment of F11R mediated pathological disorders. Thus, the present invention provides methods of treating an F11R mediated disorder in a subject by administering a therapeutically effective amount of a pharmaceutical composition of the present invention.

The term "therapeutically effective amount" means the dose required to treat an F11R-mediated disorder.

By "an F11R-mediated disorder" is meant a pathological disorder, the onset, progression or the persistence of the symptoms of which requires the participation of F11R molecules. Particularly, F11R-mediated disorders contemplated by the present invention include thrombosis, atherosclerosis, heart attacks and strokes. In addition, the inventors have determined that collagen-induced platelet aggregation and secretion can be blocked completely by the F11R peptides of the present invention.

Accordingly, "an F11R-mediated disorder" also contemplates excessive bleeding as may occur following a wound injury. Furthermore, and in accordance with the present invention "an F11R-mediated disorder" can include inflammatory diseases of the nervous system.

The term "treatment" or "treat" refers to effective inhibition, suppression or cessation of the F11R activity so as to prevent or delay the onset, retard the progression or ameliorate the symptoms of the disorder.

The term "subject" refers to any mammalian subject. Preferably, the subject is a human.

The present invention thus provides methods of interfering with, blocking or otherwise preventing the interaction or binding of platelets with endothelial cells by employing the F11R antagonists contemplated by the present invention.

The F11R antagonist peptides of the present invention (or homologs, analogs or fragments) can be used to raise single-chain antibodies (SAb) or humanized monoclonal antibodies useful in the invention. The peptides can be coupled to a carrier protein such as KLH as described in Ausubel et al. (1989) *Current Protocols in Molecular Biology*, John Wiley & Sons, New York. The KLH-antagonist peptide is mixed with Freund's adjuvant and injected into guinea pigs, rats, donkeys and the like or preferably into rabbits. Antibodies can be purified by peptide antigen affinity chromatography.

A single-chain antibody (SAb) is created by fusing together the variable domains of the heavy and light chains using a short peptide linker, thereby reconstituting an antigen binding site on a single molecule. Such single-chain antibody variable fragments (Fvs) can be fused to all or a portion of the constant domains of the heavy chain of an immunoglobulin molecule, if necessary. The use of sAb avoids the technical difficulties in the introduction of more than one gene construct into host cells. Single chain antibodies and methods for their production are known in the art. See, e.g., Bedzyk et al. (1990) *J. Biol. Chem.*, 265: 18615; Chaudhary et al. (1990) *Proc. Natl. Acad. Sci.*, 87:9491; U.S. Pat. No. 4,946,778 to Ladner et al.; and U.S. Pat. No. 5,359,046 to Capon et al.

Monoclonal antibodies can be prepared using F11R antagonist peptides and standard hybridoma technology (see e.g. Kohler et al., (1975) *Nature* 256:495; Hammerling et al., (1981) *In Monoclonal Antibodies and T Cell Hybridomas*, Elsevier, New York). For example, monoclonal antibodies to F11R antagonist peptides (homologs, analogs or fragments thereof) can be raised in Balb/C or other similar strains of mice by immunization with purified or partially purified preparations of F11R antagonist peptides. The spleens of the mice can be removed, and their lymphocytes fused to a mouse myeloma cell line. After screening of hybrids by known techniques, a stable hybrid will be isolated that produces antibodies against F11R antagonist peptides. The monoclonal antibody can be examined for its ability to inhibit the biological activity of F11R, e.g. platelet aggregation. Once produced, monoclonal antibodies are tested for specific F11R recognition by Western blot or immunoprecipitation analysis (by methods described in Ausubel et al., supra). Antibodies which antagonize F11R/platelet aggregation are considered to be useful antagonists in the invention.

The monoclonal antibodies of the present invention can be humanized to reduce the immunogenicity for use in humans. One approach is to make mouse-human chimeric antibodies having the original variable region of the murine mAb, joined to constant regions of a human immunoglobulin. Chimeric antibodies and methods for their production are known in the art. See, e.g., Cabilly et al., European Patent Application 125023 (published Nov. 14, 1984); Taniguchi et al., European patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Robinson et al., International Patent Publication #PCT/US86/02269 (published 7 May 1987); Liu et al., *Proc. Natl. Acad. Sci. USA* 84:3439-3443 (1987); Sun et al., *Proc. Natl. Acad. Sci. USA* 84:214-218 (1987); Better et al., *Science* 240:1041-1043 (1988). These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

The invention is further illustrated by the following specific examples which are not intended in any way to limit the scope of the invention.

EXAMPLE 1

Human Platelets

Whole blood was collected into the anticoagulant ACD (pH 4.6), as detailed (Kornecki et al. (1990) *J. Biol. Chem.*, 265:10042-10048, incorporated herein by reference). Platelets were washed and isolated by differential centrifugation, and resuspended in a Tyrode-albumin (0.35%) solution buffered with 11.9 mM sodium bicarbonate (pH 7.35) in the presence of apyrase, heparin, and $PGE_1$ (Id.). Final platelet suspensions did not contain any inhibitors. Platelet aggregation was measured in a Chronolog Whole Blood Lumi-Aggregometer (Chronolog Corp. Havertown, Pa.). Potentiation of platelet aggregation was measured by adding a mixture of two platelet agonists, each at a sub-threshold concentration that did not induce any platelet aggregation. The lowest concentration of each agonist which caused platelet aggregation was determined in these experiments for each donor on the day of blood collection.

Immunoblotting.

Polyacrylamide gel electrophoresis, immunoblotting of transferred proteins onto nitrocellulose strips, and detection using ECL chemluminescence were performed as detailed (Kornecki et al. (1990) *J. Biol. Chem.*, 265:10042-10048).

Antibodies.

Monoclonal antibody M.Ab.F11 (IgG1 isotype) was affinity-purified as described (Kornecki et al. (1990) *J. Biol. Chem.*, 265:10042-10048). Histidine antibody was obtained from InVitrogen (Carlsbad, Calif.).

Construction of the Plasmid pcDNA3.1/F11R.

A 726-base-pair fragment (nucleotide-6 till+720) was amplified by PCR using a human F11 receptor cDNA as a template (Sobocka et al. (1997) *Blood*, 90(10): Supp. 1, Part 2, 2996a, incorporated herein by reference) utilizing the forward primer [GCGGGATCCATCGCGATGGGGA- CAAAGGCG (SEQ ID NO: 8)], and the reverse primer [CCGACCTCGAGCGGCATTCCGCTCCACAGCTTC-CAT (SEQ ID NO: 9)] (bases in bold represent BamHI and XhoI sites), respectively. This PCR fragment encodes amino acids ser-1 to asn-208 of F11R, and excludes the C-terminal transmembrane and cytoplasmic domains. The 726-base-pair PCR-product was subcloned into plasmid pcDNA3.1/Myc-His (+) C (Invitrogen, Carlsbad, Calif.) using BamHI and XhoI to yield pcDNA3.1/F11R. Transcription of the F11R in this plasmid is under the control of CMV immediate-early promoter. The construct pcDNA3.1/F11R was verified by sequencing and fine restriction mapping prior to its use in expression studies in COS-7 cells.

Recombinant DNA Methods.

E. coli transformation, plasmid DNA isolation, restriction analysis, extraction of DNA from agarose gels and ligation of insert into pcDNA3.1/myc-His(+)C vector were carried out as described (Sambrook et al. *Molecular Cloning: A Laboratory Manuel 2nd Ed. Cold Spring Harbor Laboratory*, Cold Spring Harbor, N.Y. 1989, incorporated herein by reference). Plasmids were isolated from *E. coli* DH5α (Life Technologies, Grand Island, N.Y.) using Qiaprep columns (Qiagen, Valencia, Calif.). DNA restriction fragments were separated by agarose gel eletrophoresis and isolated with the QIAquick Gel extraction kit (Qiagen). PCR was performed using the Perkin Elmer Gene Amp 2400PCR System. DNA sequencing was performed by PCR-cycle sequencing using ABI PRISM Dye Terminator Cycle Sequencing Kit from Perkin Elmer (Foster City, Calif.) and the ABI Prism 377 DNA Squencer. Computer analysis of sequence data was performed with the Biology WorkBench, release 3.2.

Transfection of COS-7 Cells.

COS-7 cells were grown in DMEM/10% FBS (Cellgro Mediatech, Inc.) and 1% antimycotic (Life Technologies), at 37° C./5% $CO_2$. Cells (about 50% confluency), plated in a 75 mm flask, were used for transfection one day later. The plasmid pcDNA3.1/F11R (10 μg) was transfected into cells using 30 μl of FuGENE-6 (Roche Diagnostics). Cells were maintained at 37° C./5% $CO_2$ in 7 ml complete medium. Cells were also treated with FuGENE-6 alone as controls. Total RNA was isolated (RNeasy Mini Kit, Qiagen) and used for subsequent RT-PCR. RNA (2 μg) was used for reverse transcription (Omniscript Reverse Transcriptase, Omniscript RT Kit, Qiagen). Half of the reaction mixture was used to amplify F11R in a 35-cycle PCR using the specific F11R primers as detailed previously (Sobocka, supra). PCR cycling was as follows: 94° C. for 5 min followed by 35 cycles of 94° C. for 45 sec, 55° C. for 45 sec, 72° C. for 2 min and 94° C. for 2 min. A 726-bp fragment was obtained only from pcDNA3.1/F11R transfected cells. Conditioned media, collected 72 h posttransfection, were pooled and passed twice over a M.Ab.F11-immunoaffinity column. After washing of the affinity column, the bound sF11R was eluted by use of 50 mM diethylamine (pH 11.5), fractions were collected into 1 M Tris-HCl buffer (pH 8.0) and immediately dialysed against 10 mM Tris-HCl buffer (pH 7.4). The sF11R solution was concentrated 5× by Centricon YM-10 (Bedford, Mass.), and stored frozen at −20° C.

Synthesis of F11R-Peptides.

Five F11R peptides (95% pure) were synthesized (New England Peptides, Inc., Fitchburg, Mass.). The sequence of amino acids in these peptides and their location within the F11R molecule are shown in Table 1. Their mass was determined by MALDI-TOF DE mass spectrometry.

TABLE 1

| Peptide name | PEPTIDE SEQUENCE |
|---|---|
| F11R-peptide 1 | *SVTVHSSEPEVRIPENNPVKLSC<br>1----------------------23<br>(SEQ ID NO: 1) |
| F11R-peptide 2 | SYEDRVTFLPTGITFKSVTRED<br>55--------------------76<br>(SEQ ID NO: 2) |
| F11R-peptide 3 | WKFDQGDTTRLVEYNNKITASY<br>35--------------------56<br>(SEQ ID NO: 3) |
| F11R-peptide 4 | KSVTREDTGTYTC<br>70-----------82<br>(SEQ ID NO: 4) |
| F11R-peptide 5 | EQDGSPPSEYTWFKD<br>128------------142<br>(SEQ ID NO: 5) |

The amino acid numbers refer to the sequence of the mature platelet cell surface F11 receptor and of the recombinant protein, sF11R, which does not include the leader peptide sequence.
*In accordance with the present invention, ser-1 is the first amino acid that follows the 27 amino acid leader peptide sequence of the nascent protein (Sobocka et al. (2000) *Blood* 95:2600-2609).

Platelet Adhesion to an Immobilized Matrix.

An adhesion assay, based on the determination of cell-derived protein using Bicinchoninic Acid (BCA) protein assay (Tuszynski et al. (1990) *Anal. Biochem* 184:189-191, incorporated herein by reference), was used for platelet adhesion to immobilized M.Ab.F11. Wells of a 96-well plate (Nunc-Immuno™ Plate, MaxiSorp™ Surface, flat bottomed) were incubated overnight at 4° C. with 150 ml of a 1 mg/ml solution of M.Ab.F11. Wells were aspirated, washed, treated with TBS/1% BSA for 1 h at 37° C., and washed with TBS/0.1 mM $MnCl_2$/0.1 mM $CaCl_2$. Isolated platelet suspensions (100 μl) ($3×10^8$/ml) were added and plates were incubated at 37° C. for 90 min. Total platelet-associated protein was determined by dissolving the attached platelets directly with 100 μl BCA. Platelets were incubated at 37° C. for 2 h, and absorbance (595 nm) determined (Dynatech Laboratories, Chantilly, Va.).

3D-Structure of Human sF11R.

The crystal structure of the external domain of mouse recombinant JAM (Kostrewa et al. (2001) *The Embo J.* 20:4391-4398, incorporated herein by reference) was used as a template to generate a 3D model of the human recombinant sF11R based on the sequence (Sobocka et al. (2000) *Blood* 95:2600-2609, incorporated herein by reference) of the mature human platelet F11R (GenBank accession #AF207907).

EXAMPLE 2

Preparation and Use of Recombinant sF11R

A secreted, recombinant F11R protein (sF11R) was prepared in COS-7 cells which contained only the extracellular portion (amino acids ser-1 to asn-208) of the mature F11R molecule. The transcription of the recombinant sF11R in COS-7 cells was determined by RT-PCR. A 726-base-pair fragment was detected only in pcDNA3.1/F11R transfected cells. (Babinska et al. (2002) *Thromb. Haemost* 87:712-721, incorporated herein by reference). To determine the expression of sF11R in COS-7 cells, the conditioned media obtained from transfected cells were examined by immunoblotting using both a polyclonal anti-F11R antibody and the monoclonal M.Ab.F11. The sF11R polypeptide was detected in the F11R COS-7 conditioned media obtained from these two separate F11R secreting clones, COS-7 cells which were treated with only Fugene 6 (mock-transfected), or COS-7 cells transfected with a plasmid lacking F11R DNA, did not secrete sF11R. The sF11R protein was engineered to contain a Histidine tag sequence, and indeed, it was recognized by an anti-His antibody. The use of a control protein (Positope, 53 kD, obtained from InVitrogen) that contains the His tag, confirmed this identification. Finally, sF11R was purified from COS-7 cell media using M.Ab.F11 immunoaffinity chromatography. The purified sF11R was recognized by both the platelet stimulatory monoclonal antibody, M.Ab.F11, and by a polyclonal F11R antibody, directed against the N-terminal amino acids ser-1 to cys-23. The results detailed above demonstrate that transfected COS-7 cells not only synthesize by also secrete sF11R.

EXAMPLE 3

Inhibitory Effects of the Soluble Extracellular Portion of F11R ("sF11R"), and Specific Peptides Derived Thereof The soluble polypeptide sF11R was tested in the platelet aggregation assay to determine its effect on the rate and extent of platelet aggregation.

We observed that intact sF11R effectively inhibited M.Ab.F11 (2.45 µg/ml)-induced platelet aggregation at two concentrations, 1 µg/ml (FIG. 1A) and 4 µg/ml (FIG. 1B). Thus, sF11R appears to possess one or more inherent structural features, i.e., peptide sequences that participate in platelet aggregation and adhesion.

EXAMPLE 4

Inhibition of the Potentiation of Agonist-Induced Platelet Aggregation by F11R-Specific Peptides The presence of low, non-aggregating (sub-threshold) concentrations of the physiological agonist ADP, collagen or thrombin can cause platelet aggregation when added together with non-aggregating concentrations of M.Ab.F11 (Sobocka et al. (1997); (Sobocka (1998) *PhD Thesis*, SUNY Downstate Medical School, Brooklyn, N.Y. Jun. 10, 1998, published Sep. 15, 1998); (Sobocka et al. 2001, supra, incorporated herein by reference). Such potentiating effects of M.Ab.F11 on agonist-induced aggregation are depicted in FIG. 2. When sub-threshold concentrations of ADP (0.5 µM) alone (FIG. 2A) or M.Ab.F11 (0.3 µg/ml) (FIG. 2B), respectively, were added separately to platelet suspensions, there was no aggregation (low flat baseline tracing shown in panels A and B). However, when sub-threshold concentrations of ADP were added together with sub-threshold concentrations of M.Ab.F11, a pronounced aggregation response was observed, reflecting the potentiating effect (see "M.Ab.F11 plus ADP" tracings in each panel). Similar potentiating effects were observed with sub-threshold levels of thrombin or collagen (data not shown). Synthetic peptides according to published sequences of F11R were prepared.

The domains within F11R that participate in M.Ab.F11-induced platelet aggregation were identified by the method of Naik et al. (1995) *Biochem. J.* 311:155-162, incorporated herein by reference. See Table 1.

Figure 2A:
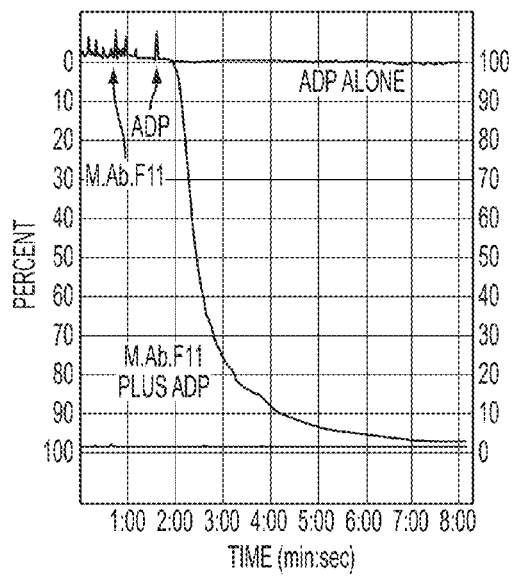
FIG. 2 illustrates the assay for the potentiation of ADP-induced platelet aggregation by sub-threshold, i.e., non-aggregating, amounts of M.Ab.F11 and adenosine diphosphate ("ADP"). The platelets do not aggregate in the presence of sub-threshold (i.e., non-aggregating) concentrations of either ADP alone (0.5 μM) or M.Ab.F11 alone (0.3 μg/ml) (see the flat recordings in FIG. 2A-B, respectively). However, in combination, the sub-threshold amounts of ADP and M.Ab.F11 induce full blown aggregation recordings as shown in FIGS. 2A-B (tracings labeled M.Ab.F11 plus ADP). Further, the aggregation-inhibiting activity of two specific F11R-derived peptides corresponding to SEQ ID NO: 1 and SEQ ID NO: 4 are exemplified in FIGS. 2C-D, respectively.
As shown in FIG. 2D, experiments were carried-out in which the peptide of SEQ ID NO: 1 (50 μM) was preincubated with platelets for about 30 sec prior to the addition of M.Ab.F11 (0.3 μg/ml), followed by the addition of ADP (0.5 μM).
FIG. 2C demonstrates that Peptide 4 SEQ ID NO: 4 completely inhibited aggregation (see the flat tracing labeled "plus Peptide 4"). The results of similar experiments using the peptides of SEQ ID NO: 2, SEQ ID NO: 3 and SEQ ID NO: 5 do not inhibit aggregation in the assay (Results not shown).
Figure 2B:
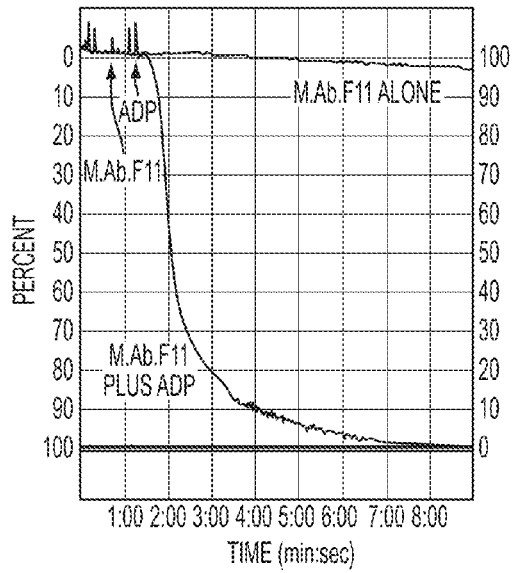
Figure 2C:
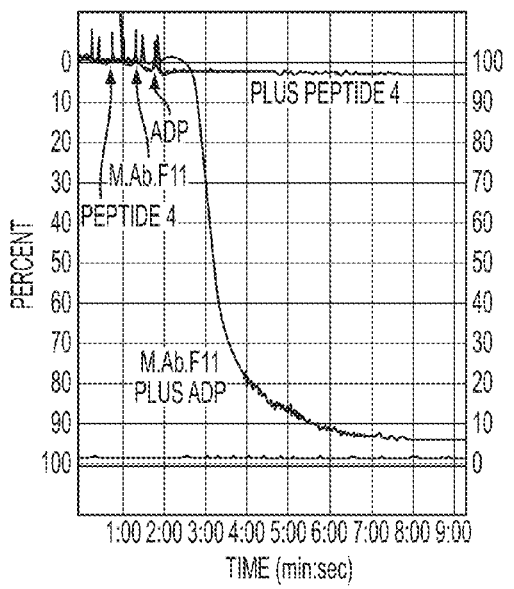
Figure 2D:
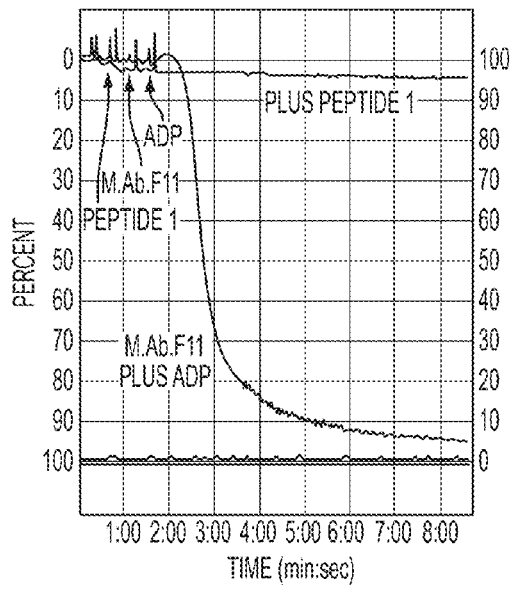

As shown in FIG. 2D, peptide 1 (SEQ ID NO: 1) (approximately 50 µM) completely inhibited the M.Ab.F11 plus ADP-induced platelet aggregation, and aggregation did not ensue when examined even after a 12 h period. In addition peptide 4 (SEQ ID NO: 4) (approximately 50 µM), was also able to completely block the M.Ab.F11 plus ADP-induced platelet aggregation (FIG. 2C). In contrast, peptides 2 (SEQ ID NO: 2), 3 (SEQ ID NO: 3), or 5 (SEQ ID NO: 5) derived from the F11R sequence (see Table 1), had no inhibitory effects on the M.Ab.F11 plus ADP-induced platelet aggregation at concentrations from approximately 50-500 µM. (Not shown).

F11R-Peptides Inhibit the Potentiation of Collagen-Induced Platelet Aggregation.

The effect of F11R peptides on M.Ab.F11-induced platelet aggregation potentiated by non-aggregating concentrations of collagen (0.5 µg/ml) was also examined and provided almost identical results to those described above and illustrated in FIG. 2A-D. Sub-threshold concentrations of collagen and of M.Ab.F11, added together, were shown to induce a strong aggregation. The sub-threshold, non-aggregating concentrations (determined separately for the platelets of each blood donor) of collagen and M.Ab.F11 did not induce platelet aggregation when added alone. However, the addition of sub-threshold amounts of collagen and M.Ab.F11 triggered a full-blown platelet aggregation. The potentiation by M.Ab.F11 of collagen-induced platelet aggregation could be completely blocked by addition of either peptide 1 (SEQ ID NO: 1) or peptide 4 (SEQ ID NO: 4). However, the peptides of SEQ ID NO: 3 and SEQ ID NO: 5 did not inhibit platelet aggregation.

The addition of sF11R (1 µg/ml) to platelet suspensions completely blocked the potentiation by M.Ab.F11 of both ADP- and collagen-induced platelet aggregation.

Thus, the results of the studies on inhibiting platelet aggregation were the same in ADP-induced aggregation as well as collagen-induced aggregation. Namely, that the sequences comprising peptides 1 (SEQ ID NO: 1) and 4 (SEQ ID NO: 4) in the F11R protein are likely to be key participants in platelet aggregation.

EXAMPLE 5

Two Specific F11R-Peptides Inhibit Platelet Adhesion to M.Ab.F11

Figure 3:
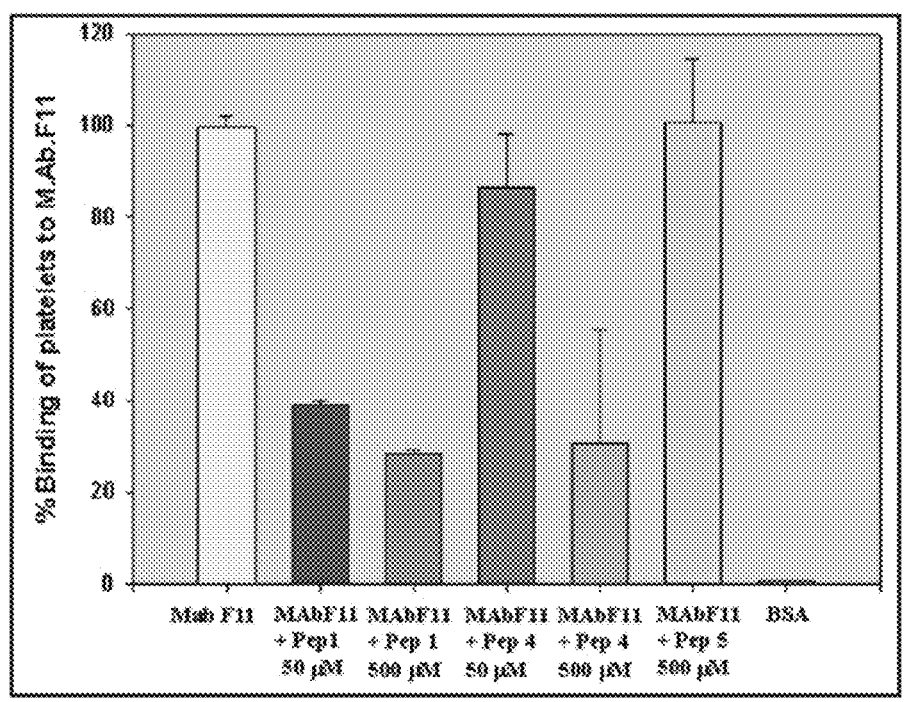
FIG. 3 shows inhibition by F11R peptides (SEQ ID NOS: 1 and 4) in a platelet adhesion assay in which monoclonal antibody M.Ab.F11 was immobilized and the binding of platelets to immobilized M.Ab.F11 was measured.

The five peptides with sequences shown in Table 1 were tested also for their effects on the adhesion of platelets to immobilized M.Ab.F11 (applied at a concentration of 150 ng/well). The left bar of FIG. 3 (labeled "M.Ab.F11") demonstrates the control adhesion measured without added peptide. Peptide 1 (SEQ ID NO: 1), added at 50 µM caused about 60% inhibition of the adhesion of platelets to immobilized M.Ab.F11, and with 500 µM of peptide 1 (SEQ ID NO: 1), about 70% inhibition was observed. Peptide 4 (SEQ ID NO: 4), at 50 µM, produced very little (10%) inhibition compared to peptide 1 (SEQ ID NO: 1) at similar concentrations. However, 500 µM of peptide 4 (SEQ ID NO: 4) produced approximately 70% inhibition in the adhesion of platelets to M.Ab.F11, similar to that observed with peptide 1 (SEQ ID NO: 1) at the same concentration. On the other hand, the addition of 500 µM (or higher) of control peptides 2, 3 or 5 did not cause significant inhibition of platelet adhesion to M.Ab.F11.

EXAMPLE 6

Fab Fragments of Monoclonal Antibody M.Ab.F11 Inhibit Platelet Aggregation Induced by M.Ab.F11

The F11R/JAM-A receptor is constitutively expressed on the surface membrane of human platelets. Studies were carried out testing the effects of Fab fragments prepared from M.Ab.F11, i.e., on the M.Ab.F11-induced platelet aggregation that is triggered by M.Ab.F11 binding to F11R. It was determined that these Fab fragments interfered with the ability of the intact M.Ab.F11 antibody to activate platelets through the constitutively-expressed F11R.

Figure 4A:
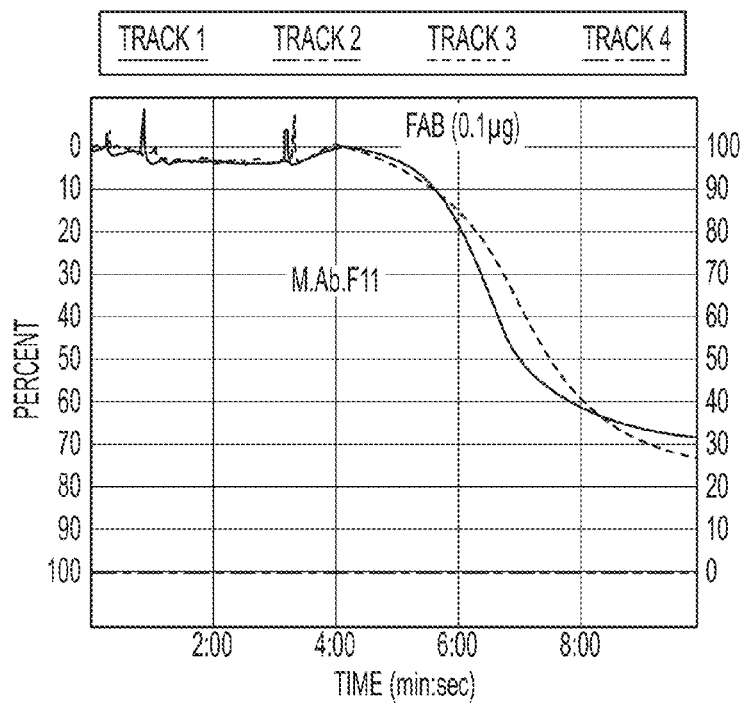
FIGS. 4a and 4b illustrate the inhibitory effects of two concentrations of Fab fragments prepared from monoclonal antibody M.Ab.F11 in the platelet aggregation assay. The Fab fragments were added at concentrations of 0.1 μg/ml (a low concentration) (panel a) (FIG. 4a) or 1.0 μg/ml, (panel b) (FIG. 4b), a 10-fold higher concentration which completely inhibited platelet aggregation.
Figure 4B:
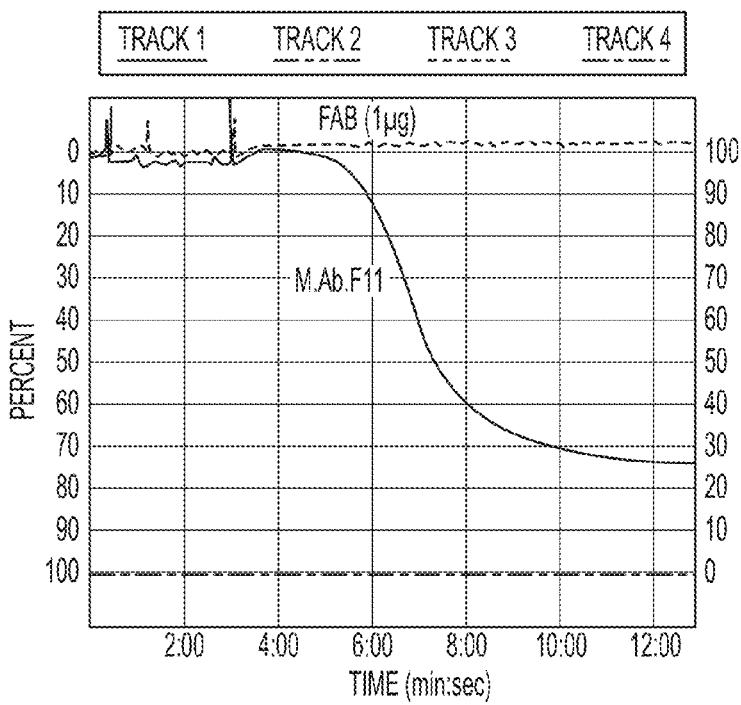

As shown below, platelet aggregation was assayed in the presence of either 0.1 µg/ml (FIG. 4a), or 1.0 µg/ml (FIG. 4b). At a concentration of 1.0 µg/ml (panel b), the Fab fragments completely inhibited the induction of platelet aggregation induced by the intact stimulatory monoclonal antibody M.Ab.F11 (approximately 1 µg/ml) (FIG. 4b). A ten-fold decrease in the concentration of Fab fragments (approximately 0.1 µg/ml) was far less effective (FIG. 4a) indicating a dose dependent relationship between the concentration of Fab fragments and the extent of platelet aggregation. It has also been observed that the sensitivity of platelets to Fab inhibition of platelet aggregation could vary among different individuals. Interestingly, the more sensitive the platelet preparation was to M.Ab.F11-induced platelet aggregation, the more sensitive the platelets were to the Fab-mediated inhibition as well. In other words, a lower concentration of Fab fragments (lower than approximately 1 µg/ml) was sufficient to inhibit M.Ab.F11-induced platelet aggregation using the more sensitive platelets. In contrast, Fc fragments of M.Ab.F11 did not inhibit platelet aggregation by intact M.Ab.F11. The Fab fragments blocked M.Ab.F11-induced platelet aggregation competitively presumably, by inhibiting the binding of M.Ab.F11 to the extracellular domain of F11R. These results verified that the preparations of Fab used in these studies have the expected activity of inhibiting interactions of M.Ab.F11 with the F11R.

EXAMPLE 7

Inhibition of Platelet Adhesion to TNFα-Treated Endothelial Cells by Fab Fragments of M.Ab.F11

Under healthy or normal conditions, the F11R/JAM-A receptor is localized at the tight junctions of endothelial cells (ECs) comprising the endothelium. In healthy subjects platelets do not adhere to the endothelium. However, after contacting a healthy endothelium with one or more proinflammatory (i.e., inducing in the endothelium, specifically the ECs, an inflammatory state or an inflammatory condition) cytokines the localization of F11R shifts away from being concentrated in the junctional regions of the endothelium to a more uniform distribution along the cell surfaces of the ECs in the endothelium. This change in surface distribution of F11R may be referred to as the pathophysiological or inflammatory distribution, which is indicative of the endothelial cells being in an inflammatory state. Therefore, under inflammatory conditions, platelets adhere to the endothelium, in part, due to the enhanced accessibility F11R molecules on the EC surface for platelet binding.

Figure 5:
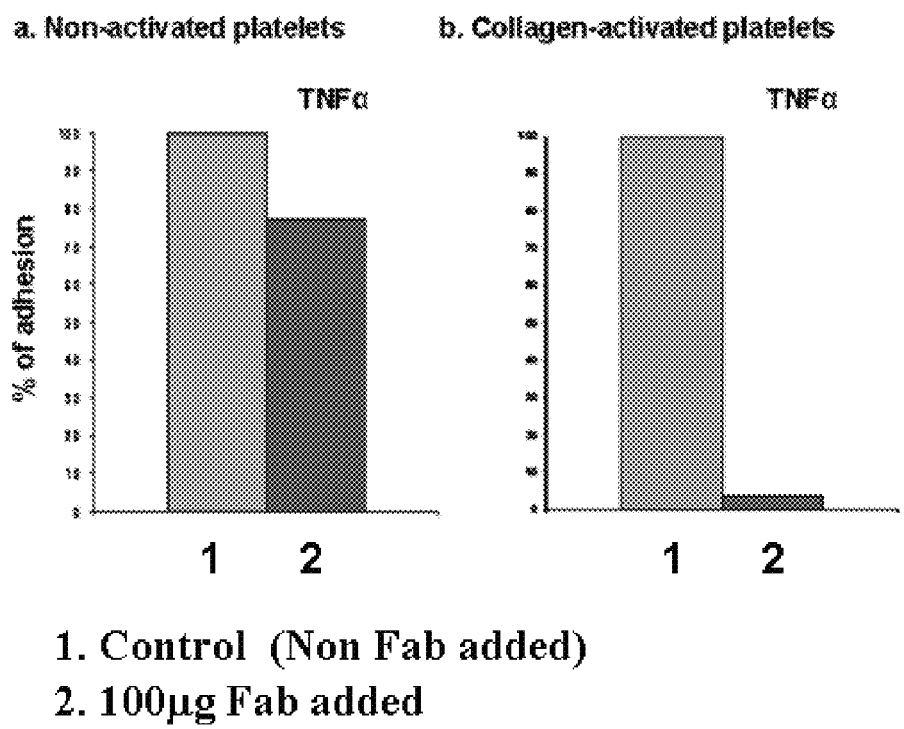
FIG. 5 illustrates Fab fragment inhibition of the adhesion of either non-activated platelets (FIG. 5A) or collagen-activated platelets (FIG. 5B) to proinflammatory cytokine, TNF-α stimulated-endothelial (HAEC, human aortic endothelial cell) monolayers.

In experiments presented below (FIG. 5), we tested the inhibitory effects of Fab fragments on the adhesion of platelets (either non-activated or activated) to human aortic endothelial cells (HAECs) after inducing an inflammatory state by contacting the endothelium with one or more cytokines. As shown in FIG. 5a, the Fab fragments inhibited the adhesion of non-activated platelets to TNFα-treated HAEC by about 20% (see FIG. 5a, BAR 2, 100 µg Fab). However, under conditions in which both the platelets were activated with the physiological agonist collagen and the HAEC were stimulated with a single treatment of TNFα, the level of inhibition was surprisingly found to be complete, i.e., very close to 100% inhibition (see FIG. 5b, BAR 2, 100 µg Fab).

EXAMPLE 8

Fab Fragments of M.Ab.F11 Inhibit the Adhesion of Platelets to HAEC that have been Treated with a Combination of Cytokines The Inhibitory Efficacy of Fab fragments on the ability of platelets to adhere to inflamed endothelial cells was assessed with HAEC monolayers that have attained an elevated level of stimulation by treating the monolayers with two cytokines, TNF-α and INF-γ, simultaneously. The use of TNF-α together with INF-γ results in the HAECs achieving a particularly high level, perhaps even near maximal, of an inflammatory state that is not achieved by treating HAEC monolayers with either TNF-α or INF-γ individually. TNF-α and INF-γ were applied simultaneously to the HAEC before measuring the adhesion of platelets to EC. Such an inflammatory condition results in the expression of maximal or near maximal F11R/JAM-A at the luminal surface of HAEC, which in turn, results in a maximal degree of adhesion of platelets to the highly stimulated and inflamed HAECs.

Figure 6:
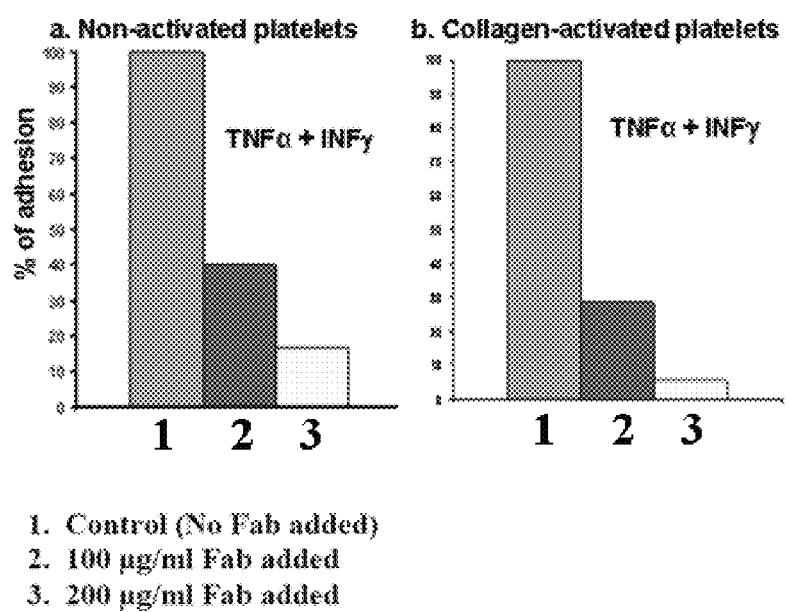
FIG. 6 illustrates inhibition by the Fab fragment of M.Ab.F11 of the adhesion of non-activated platelets (FIG. 6A), or collagen-activated platelets (FIG. 6B) to HAEC monolayers treated with a proinflammatory cytokine combination comprised of both TNF-α plus INF-γ.

As shown in FIG. 6a, a significant inhibition of the adhesion of non-activated platelets to TNF-α plus INF-γ-treated HAEC occurred in the presence of F11R Fab fragments (BAR 1, no Fab added; BAR 2, 100 µg Fab; BAR 3, 200 µg Fab). These experiments revealed that in contrast to the 20% inhibition of the aggregation of non-activated platelets to HAEC treated with the cytokine TNF-α alone, a much greater inhibition (>approximately 60%) (see FIG. 6a, BAR 2) in the adhesion of non-activated platelets was achieved under conditions in which the ECs were exposed to a combined treatment of TNF-α and INF-γ. An even greater degree of inhibition (>approximately 80%), in the adhesion of non-activated platelets to TNF-α and INF-γ-treated EC could be achieved when the concentration of Fab fragments was increased from approximately 100 µg/ml to approximately 200 µg/ml (see FIG. 6a, BAR 3). As shown in FIG. 6b, under the conditions wherein platelets were activated by collagen and the EC were stimulated with both TNF-α and INF-γ, we observed significant inhibition of the adhesion of collagen-activated platelets to cytokine-treated HAEC in the presence of Fab fragments (BAR 1, no Fab added; BAR 2, 100 µg Fab added; BAR 3, 200 µg Fab added). These experiments revealed that an even greater degree of inhibition could be achieved depending on the degree of cytokine activation of HAEC. A 70% inhibition of the adhesion of collagen-activated platelets to TNF-α plus INF-γ-treated HAEC could be achieved in the presence of approximately 100 µg Fab fragments (BAR 2), and over 90% inhibition of the adhesion of collagen-activated platelets to TNF-α plus INF-γ-treated HAEC could be achieved in the presence of approximately 200 µg Fab fragments (BAR 3).

These results indicate that Fab fragments of either murine M.Ab.F11 or Fabs of a humanized version of M.Ab.F11 can be useful as a new therapeutic for the prevention and treatment of thrombosis, atherosclerosis, heart attack and stroke.

EXAMPLE 9

The results of an in-vivo study of the effects of F11R peptide 4D on plaque formation in an animal model of atherosclerosis (apoE knockout/KO mice) are discussed below. The atherosclerosis-prone apoE KO is a strain of mice that has been genetically engineered to develop cardiovascular disease. This genetic abnormality is manifested by the continuous development of atherosclerotic plaques from early age to adulthood, accompanied by deteriorating, sickly appearance.

The study was conducted on atherosclerosis prone apoE deficient (knock-out female mice of 6 weeks of age) of a C57BL/6 background. The mice were obtained from the Jackson Laboratory (Bar Harbor, Me.). Seven animals were injected daily with peptide 4D. In parallel, control groups, consisting of animals injected with water, the vehicle used to deliver peptide 4D, was maintained. All mice were fed a Western-type diet.

Figure 7B:
FIG. 7B illustrates the physical appearance of the treated group of animals.
Figure 7A:
FIG. 7A illustrates the appearance of the untreated group of animals.
Figure 7D:
FIG. 7D illustrates the physical appearance of the treated group of animals.
Figure 7C:
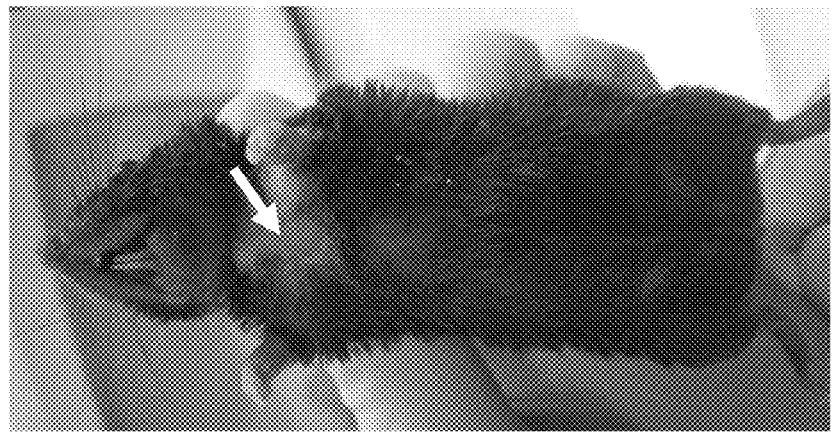
FIG. 7C illustrates the appearance of the untreated group of animals.
Figure 7F:
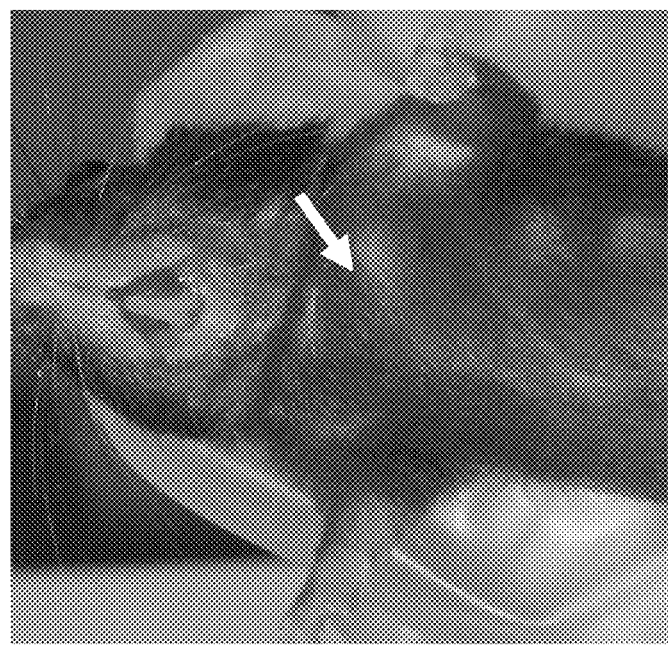
FIG. 7F illustrates the physical appearance of the treated group of animals.
Figure 7E:
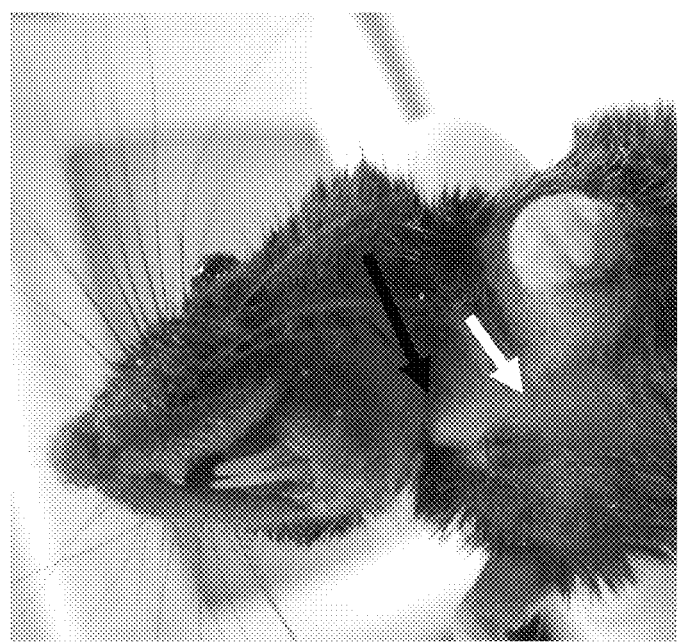
FIG. 7E illustrates the appearance of the untreated group of animals.
Figure 8A:
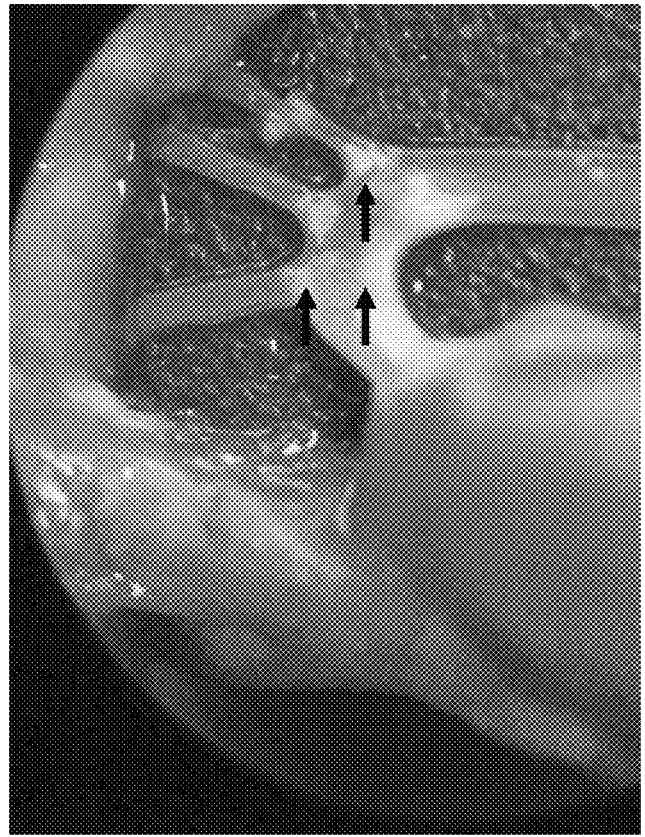
FIG. 8A illustrates a comparison of plaque formation between an untreated animal and a treated animal.
Figure 8A:
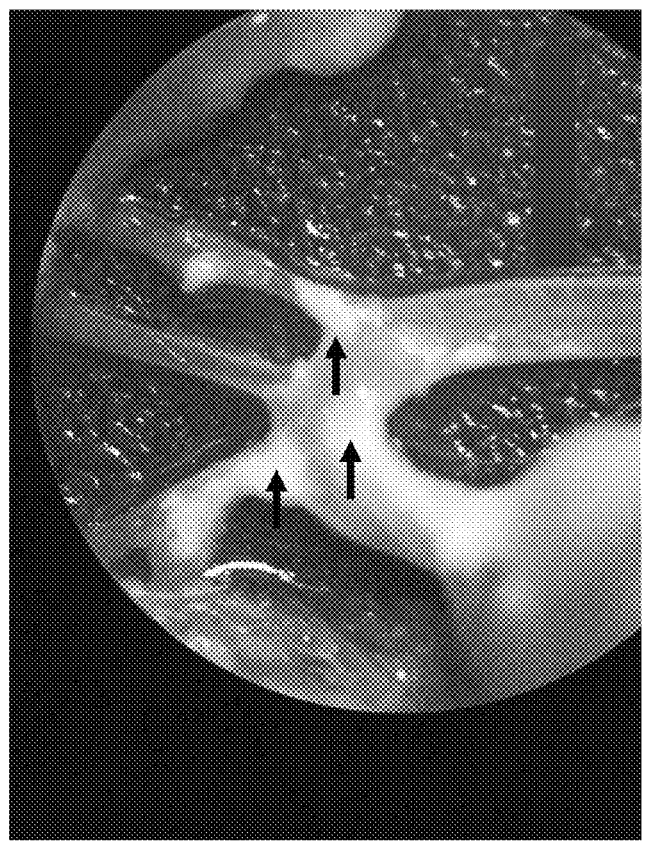
Figure 8B:
FIG. 8B illustrates a comparison of plaque formation between an untreated animal and a treated animal.
Figure 8B:
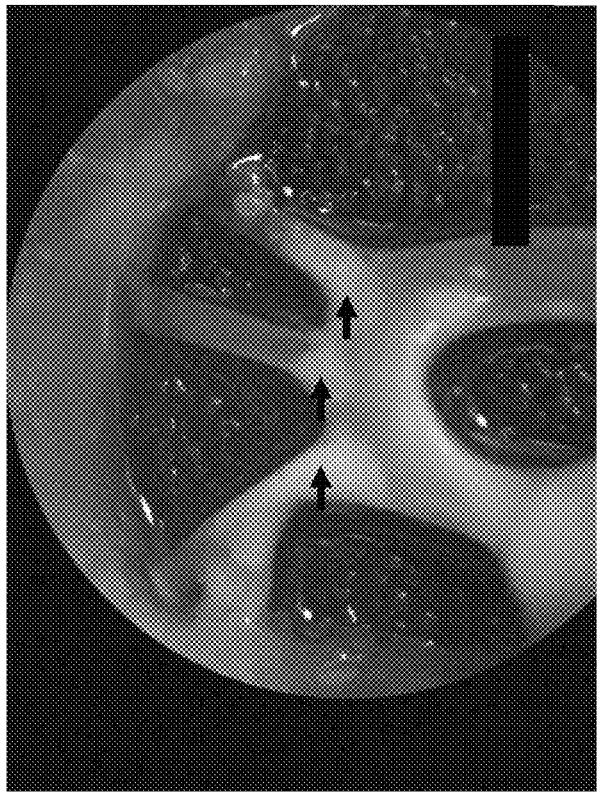
Figure 8C:
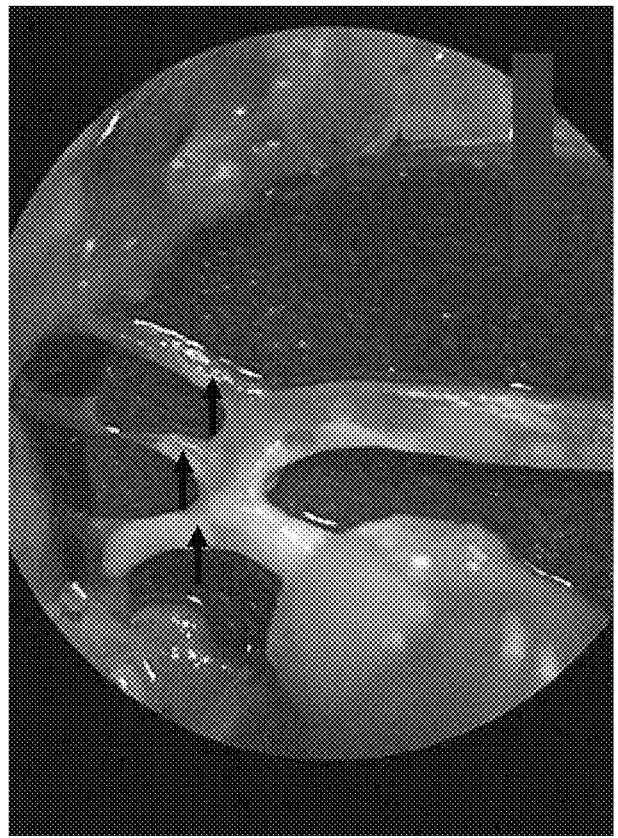
FIG. 8C illustrates a comparison of plaque formation between an untreated animal and a treated animal.
Figure 8C:
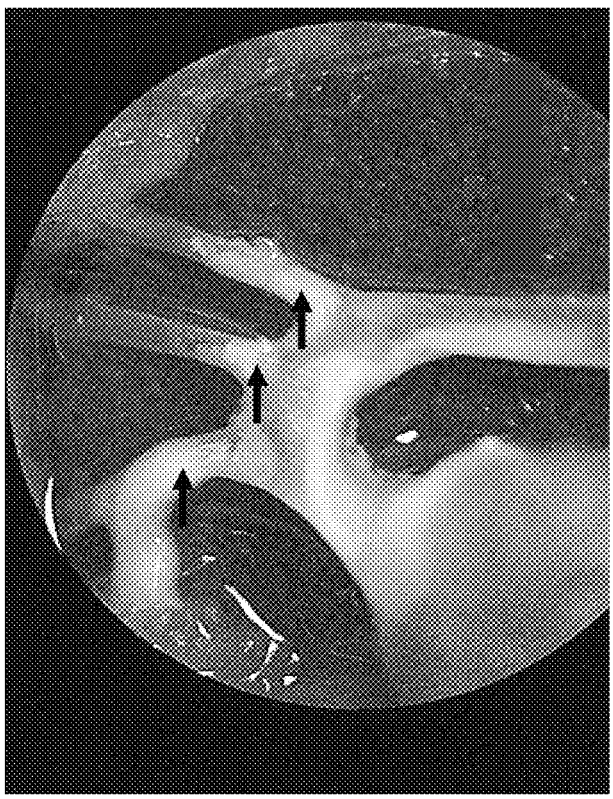
Figure 9A:
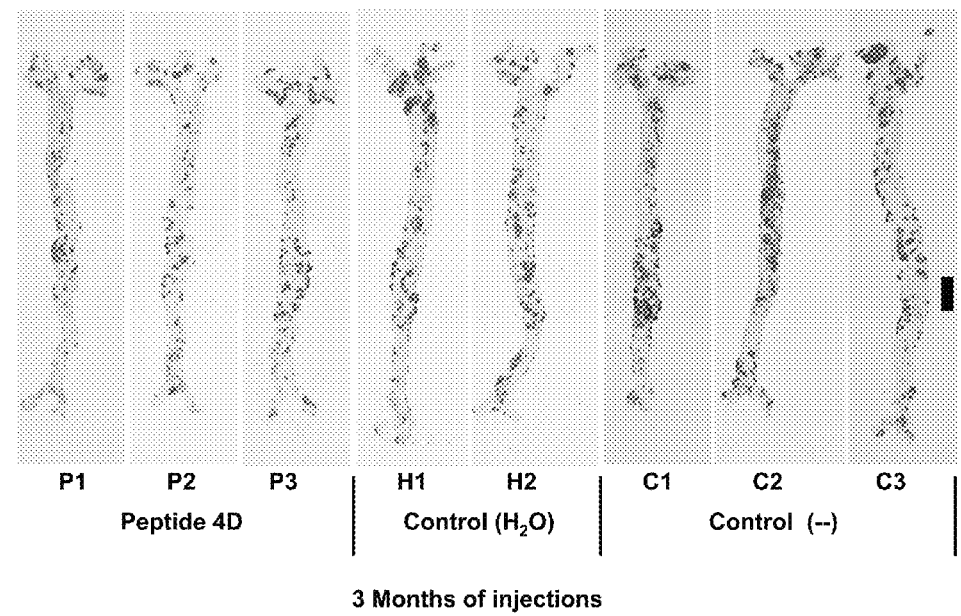
FIG. 9A illustrates a comparison of the aortae of between treated and untreated animals.
Figure 9B:
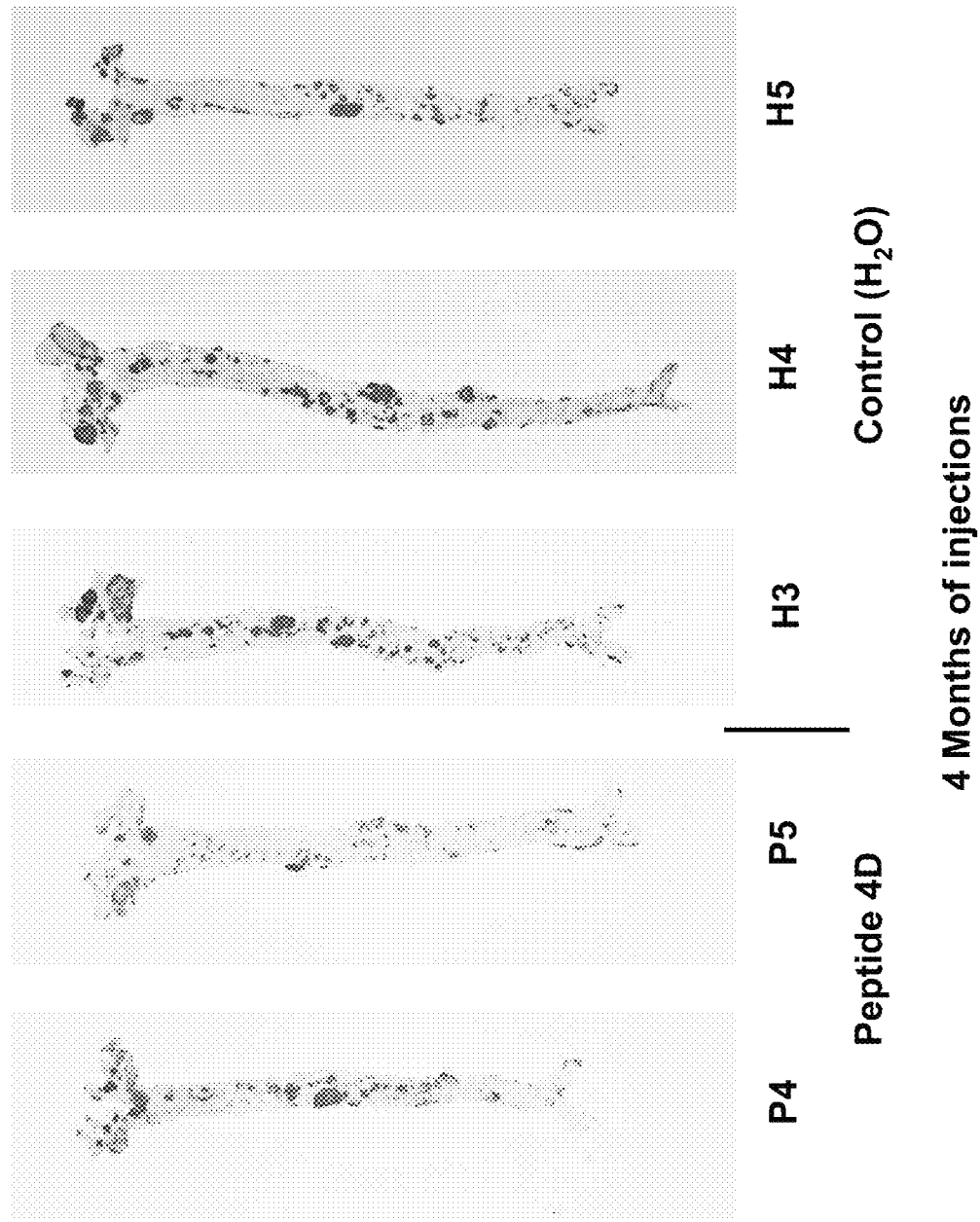
FIG. 9B illustrates a comparison of the aortae of between treated and untreated animals.
Figure 9C:
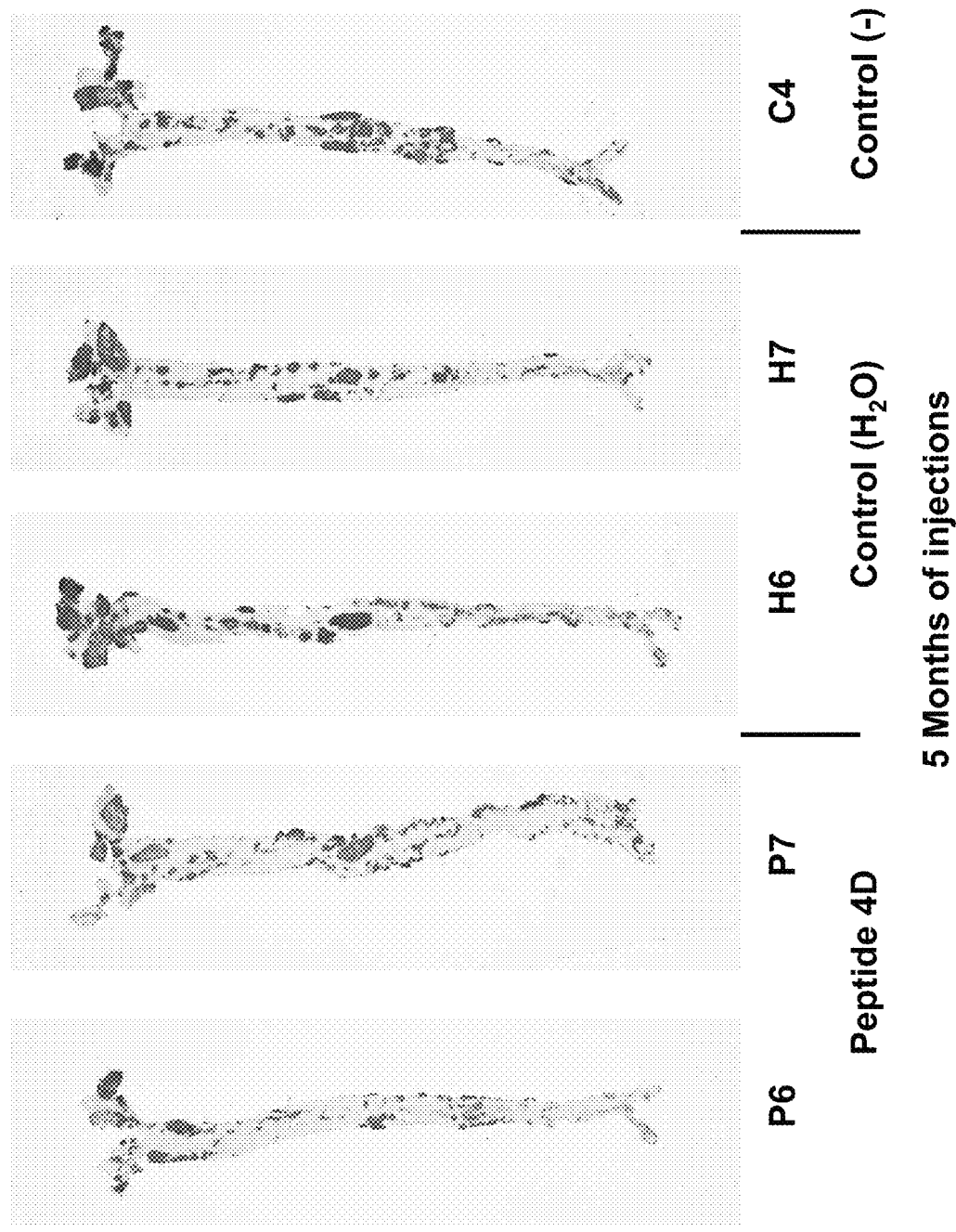
FIG. 9C illustrates a comparison of the aortae of between treated and untreated animals.
Figure 9D:
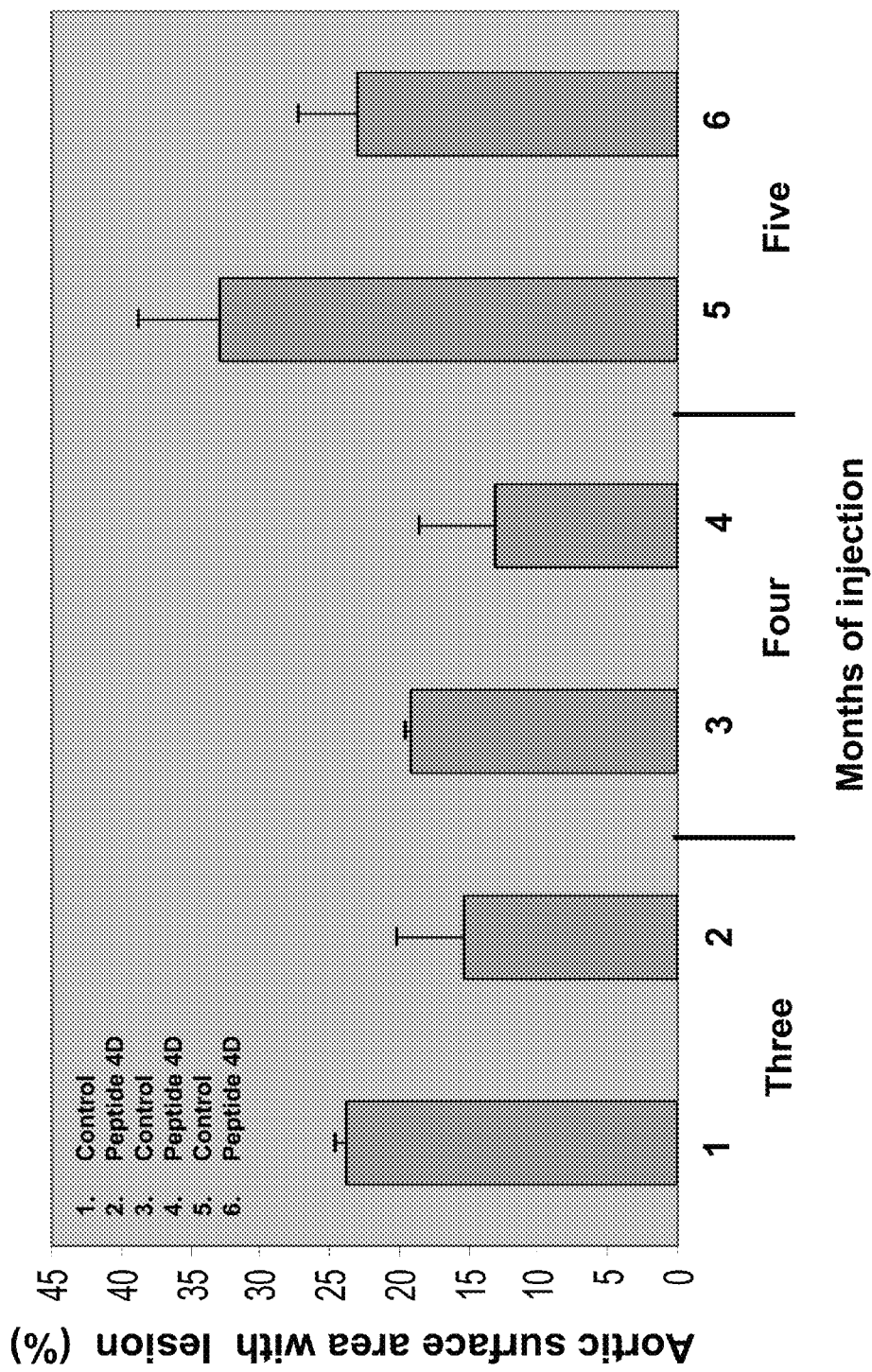
FIG. 9D illustrates a comparison of the aortic lesions between treated and untreated animals.

With the administration of the peptide 4D to the mice for a 5 month period (See FIG. 7B, "+P"), it was observed that the treatment prevented the degeneration of the animal's appearance over the same time period in which the appearance of the untreated group of animals (FIG. 7A) deteriorated. The loss of hair, itching/scratching and lesions that developed on the skin of the untreated group (See FIG. 7C, arrow) were not observed in mice treated with peptide 4D (See FIG. 7D, label "+P"). Skin lesions developed in other untreated mice as shown in FIG. 7E, whereas the mouse treated with peptide 4D demonstrated a healthy coat of hair (See FIG. 7F, label "+P").

At pre-determined intervals of 3, 4 and 5 months of treatment, the aortae were dissected. Following the dissection of the aortae of all mice, morphometric analyses of lesion areas was performed on aortic arch sections stained with Harris hematoxylin-eosin. The total intimal lesion areas were quantified by taking the average of 6 sections spaced 30 μm apart, beginning at the base of the aortic root of each animal. Images were viewed and captured with a microscope (Nikon) equipped with a color video camera (Motic Images Plus 2.0) attached to a computerized imaging system with Image-J.

Atherosclerotic lesions in the aortic arch are indicated by the arrows in FIG. 8. A comparison between the large size of the atherosclerotic plaques that developed in apoE KO mice left untreated for three months with animals that were treated with peptide 4d is depicted in FIG. 8A. In FIG. 8A, the arrows point to the three major atherosclerotic lesions/plaques within the aortic arch. FIG. 8B compares the size of plaques in untreated and treated animals following four months of injection with peptide 4D for the treated animals. FIG. 8C compares the size of plaques in untreated and treated animals following five months of injections of peptide 4D for the treated animals. The beneficial effects of treatment with peptide 4D can be observed from these figures.

En face assays (to visualize the entire aorta) were conducted for comparison of the size and number of atherosclerotic plaques in treated and untreated animals using an Oil red O staining procedure, as shown in FIG. 9. FIG. 9A illustrates the number and size of plaques which were observed in animals that were treated with peptide 4D (designated "P1, P2, P3") for a 3 month period versus animals that were not treated with peptide 4D (controls numbered "H1, H2, C1, C2, C3"). FIG. 9B illustrates the differences in the number and size of plaques in animals following a 4-month period of injection with peptide 4D, comparing animals "P4, P5" treated with peptide 4D versus controls "H3, H4, H5". FIG. 9C illustrates plaques developed in animals following a 5-month period of injections with peptide 4D, comparing treated animals "P6, P7" with control untreated animals "H6, H7, C4." The quantitation of the results of the en face assays is shown in FIG. 9D which illustrates that a decrease in the size of the atherosclerotic plaques were detectable following a 3, 4 and 5 month period of injection with peptide 4D.

Figure 10A:
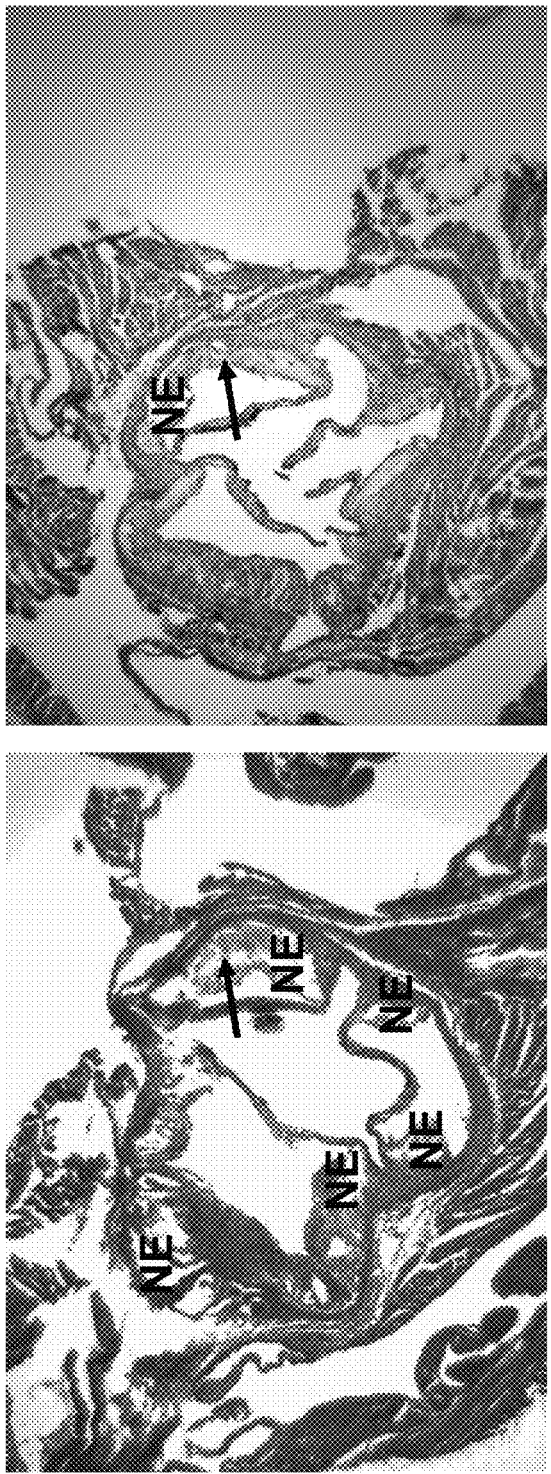
FIG. 10A illustrates a comparison between atherosclerotic plaques of treated and untreated animals.
Figure 10B:
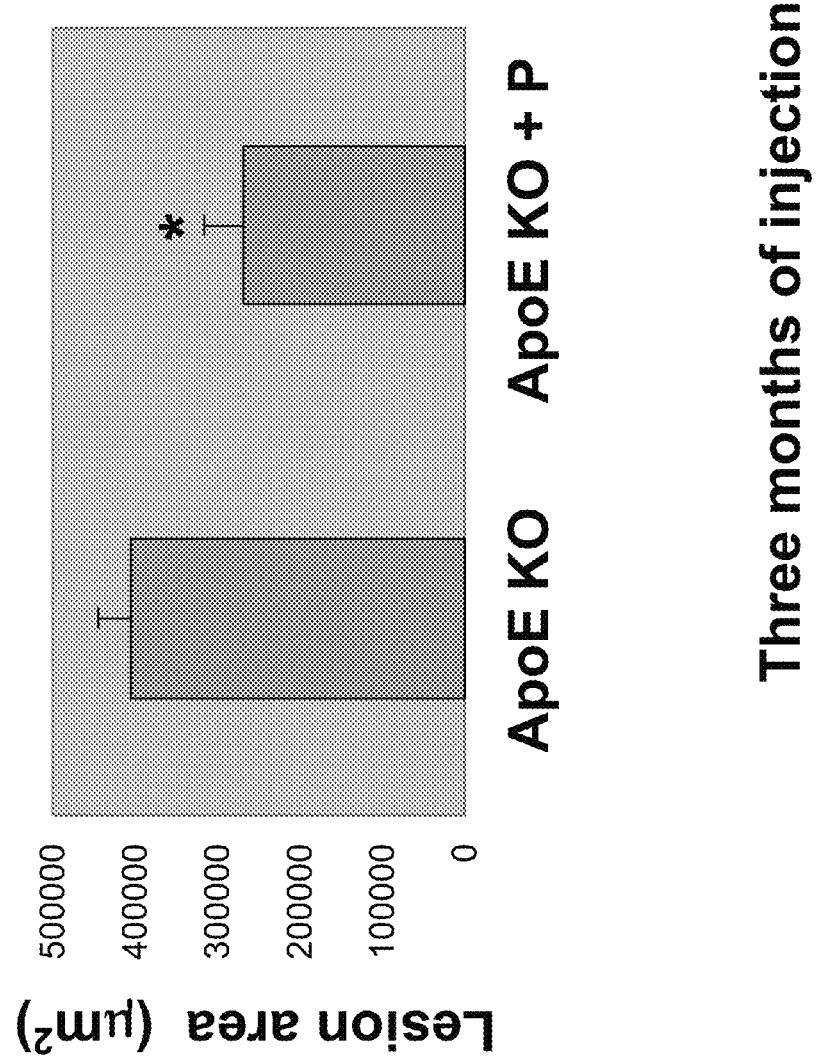
FIG. 10B illustrates a comparison between atherosclerotic lesions of treated and untreated animals.
Figure 10C:
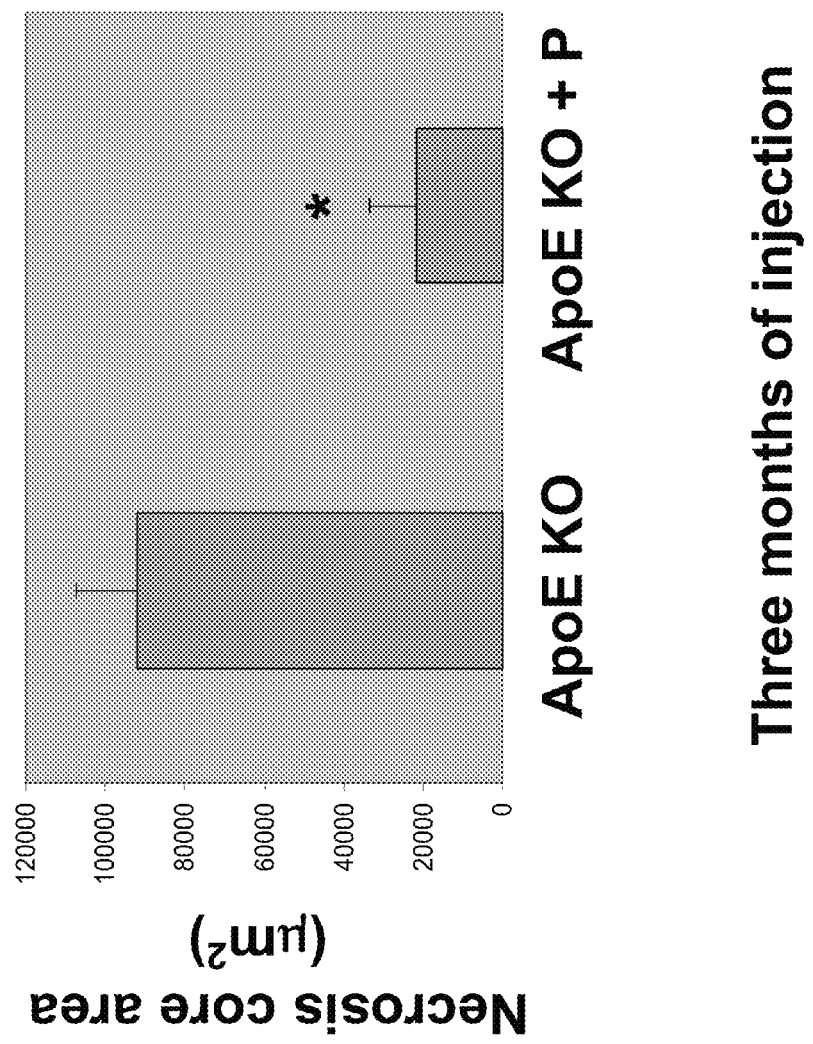
FIG. 10C illustrates a comparison between atherosclerotic lesions of treated and untreated animals.
Figure 10D:
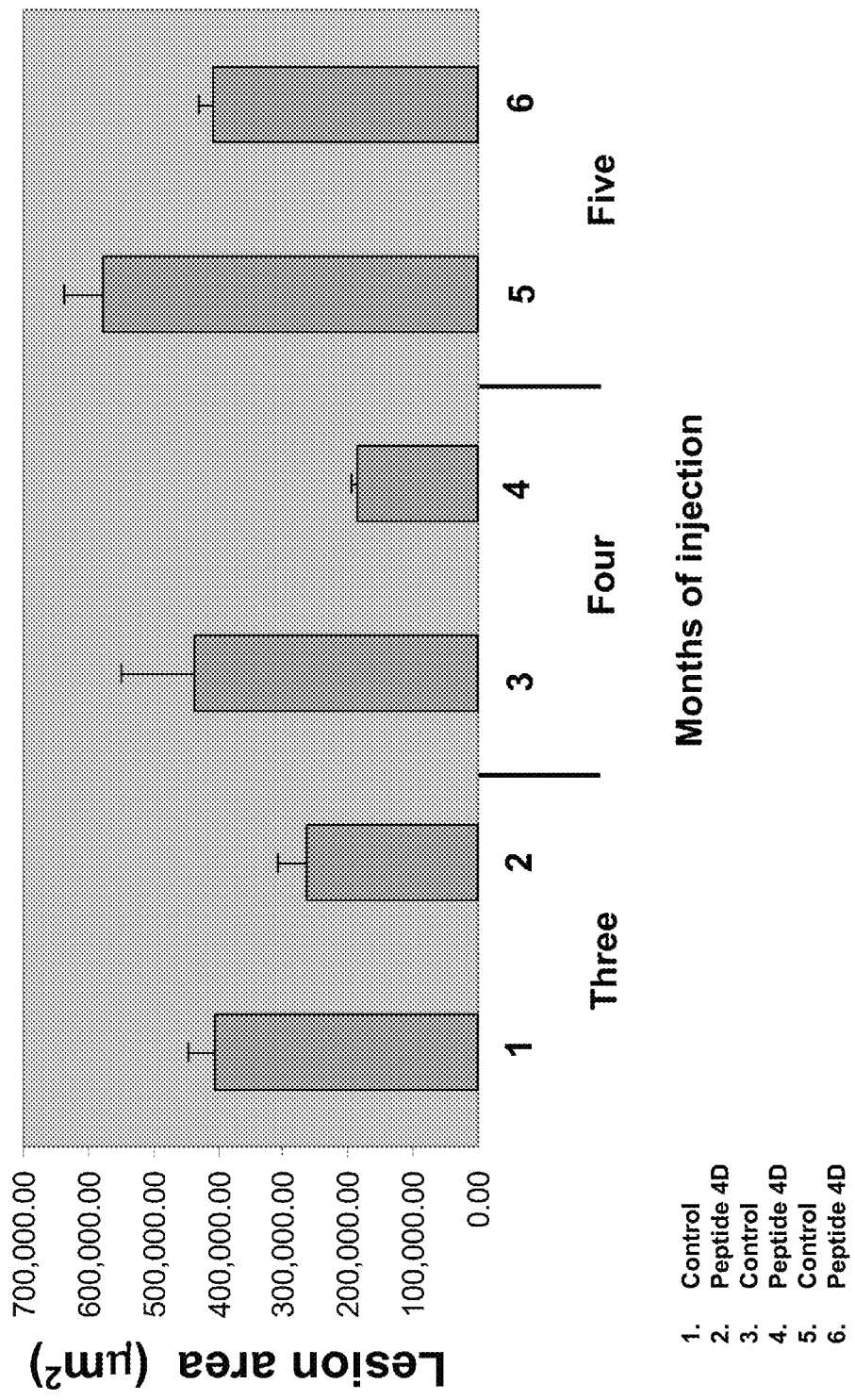
FIG. 10D illustrates a comparison between atherosclerotic lesions of treated and untreated animals.

The proximal aortae of treated an untreated groups were also assessed by hematoxylin-eosin staining of the proximal aorta (root assay) for the size of the lesions/plaques and the necrotic core area within the proximal aorta. FIG. 10A illustrates the plaques and the size of the necrotic core area of animals treated or not treated with peptide 4D for a 3 month period. An illustration of the size of the lesion area is shown in FIG. 10B, significant decrease in the size of the lesion area was observed between untreated animals and animals treated for 3 months with peptide 4D (FIG. 10B, apoE KO+P, *P<0.05). Further, as seen in FIG. 10C, a significant decrease in the size of the necrosis core area (NE) within the lesion was observed following the 3 month period of injection with peptide 4D. FIG. 4D demonstrates that significant decreases in the size of the plaque/lesion areas were observed in animals following 3, 4 and 5 months of injections with peptide 4D.

The results shown above indicate that the administration of F11R peptide 4D to apoE KO mice significantly decreases the rate and extent of atherosclerotic plaque formation in major arterial blood vessels, as shown in FIGS. 8-10, and diminishes the secondary consequences caused by atherosclerosis in the mice, including deterioration of physical appearance as can be seen in FIG. 7. The results indicate that synthetic compounds that mimic the structure and inhibitory functions of F11R peptides, such as peptide 4D, can serve as drugs for the prevention and treatment of atherosclerosis, thromboatherosclerosis, heart attacks, stroke and other human cardiovascular disorders involving inflammatory processes and plaque formation.

What is claimed is:

1. A compound comprising a peptidomimetic which interacts sterically with the binding site of a F11R molecule, wherein the peptidomimetic has a sequence selected from the group consisting of dKSVTdREDTGTYTC-CONH$_2$ (SEQ ID NO: 10), KSVTdREDTGTYTC-CONH$_2$ (SEQ ID NO: 11), SVTdREDTGTYTC-CONH$_2$ (SEQ ID NO: 12), VTdREDTGTYTC-CONH$_2$ (SEQ ID NO: 13), TdREDTGTYTC-CONH$_2$ (SEQ ID NO: 14), dREDTGTYTC-CONH$_2$ (SEQ ID NO: 15), REDTGTYTC-CONH$_2$ (SEQ ID NO: 16), EDTGTYTC-CONH$_2$ (SEQ ID NO: 17), DTGTYTC-CONH$_2$ (SEQ ID NO: 18), TGTYTC- CONH$_2$ (SEQ ID NO: 19), GTYTC-CONH$_2$ (SEQ ID NO: 20), dKSVTdREDTGTYTC (SEQ ID NO: 21), dKSVTdREDTGTYT (SEQ ID NO: 22), dKSVTdREDTGTY (SEQ ID NO: 23), dKSVTdREDTGT (SEQ ID NO: 24), dKSVTdREDTG (SEQ ID NO: 25), dKSVTdREDT (SEQ ID NO: 26), dKSVTdRED (SEQ ID NO: 27), dKSVTdRE (SEQ ID NO: 28), dKSVTdR (SEQ ID NO: 29), dKSVTd (SEQ ID NO: 30) and dKSVT (SEQ ID NO: 31).

* * * * *

SEQUENCE LISTING

<160> NUMBER OF SEQ ID NOS: 68

<210> SEQ ID NO 1
<211> LENGTH: 23
<212> TYPE: PRT
<213> ORGANISM: Artificial Sequence
<220> FEATURE:
<223> OTHER INFORMATION: Synthetic peptide

<400> SEQUENCE: 1

Ser Val Thr Val His Ser Ser Glu Pro Glu Val Arg Ile Pro Glu Asn
1               5                   10                  15

-continued

Asn Pro Val Lys Leu Ser Cys
            20

<210> SEQ ID NO 2
<211> LENGTH: 22
<212> TYPE: PRT
<213> ORGANISM: Artificial Sequence
<220> FEATURE:
<223> OTHER INFORMATION: Synthetic peptide

<400> SEQUENCE: 2

Ser Tyr Glu Asp Arg Val Thr Phe Leu Pro Thr Gly Ile Thr Phe Lys
1               5                   10                  15

Ser Val Thr Arg Glu Asp
            20

<210> SEQ ID NO 3
<211> LENGTH: 22
<212> TYPE: PRT
<213> ORGANISM: Artificial Sequence
<220> FEATURE:
<223> OTHER INFORMATION: Synthetic peptide

<400> SEQUENCE: 3

Trp Lys Phe Asp Gln Gly Asp Thr Thr Arg Leu Val Glu Tyr Asn Asn
1               5                   10                  15

Lys Ile Thr Ala Ser Tyr
            20

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide

<400> SEQUENCE: 4

Lys Ser Val Thr Arg Glu Asp Thr Gly Thr Tyr Thr Cys
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

Glu Gln Asp Gly Ser Pro Pro Ser Glu Tyr Thr Trp Phe Lys Asp
1               5                   10                  15

<210> SEQ ID NO 6
<211> LENGTH: 1816
<212> TYPE: DNA
<213> ORGANISM: Homo sapiens

<400> SEQUENCE: 6
agtggcctga tcgcgatggg gacaaaggcg caagtcgaga ggaaactgtt gtgcctcttc      60
atattggcga tcctgttgtg ctccctggca gggcagtgtt acagtgcact cttctgaacc    120
tgaagtcaga attcctgaga ataatcctgt gaagttgtcc tgtgcctact cgggcttttc    180
ttctccccgt gtggagtgga agtttgacca aggagacacc accagactcg tttgctataa    240
taacaagatc acagcttcct atgaggaccg ggtgaccttc tgccaactg gtatcacctt    300

| | |
|---|---|
| caagtccgtg acacgggaag acactgggac atacacatgg tctctgagga aggcggcaac | 360 |
| agctatgggg aggtcaaggt caagctcatc gtgcttgtgc ctccatccaa gcctacagtt | 420 |
| aacatcccct cctctgccac cattgggaac cgggcagtgc tgacatgctc agaacaagat | 480 |
| ggttccccac cttctgaata cacctggttc aaagatggga tagtgatgcc tacgaatccc | 540 |
| aaaagcaccc gtgccttcag caactcttcc tatgtcctga atcccacaac aggagagctg | 600 |
| gtctttgatc ccctgtcagc ctctgatact ggagaataca gctgtgaggc acggaatggg | 660 |
| tatgggacac ccatgacttc aaatgctgtg cgcatggaag ctgtggagcg aatgtgggg | 720 |
| gtcatcgtgg cagccgtcct tgtaaccctg attctcctgg gaatcttggt ttttggcatc | 780 |
| tggtttgcct atagccgagg ccactttgac agaacaaaga aagggacttc gagtaagaag | 840 |
| gtgatttaca gccagcctag tgcccgaagt gaaggagaat caaacagac ctcgtcattc | 900 |
| ctggtgtgag cctggtcggc tcaccgccta tcatctgcat ttgccttact caggtgctac | 960 |
| cggactctgg ccctgatgt ctgtagtttc acaggatgcc ttatttgtct tctacacccc | 1020 |
| acagggcccc ctacttcttc ggatgtgttt taataatgt cagctatgtg ccccatcctc | 1080 |
| cttcatgccc tccctccctt tcctaccact gctgagtggc ctggaacttg tttaaagtgt | 1140 |
| ttattcctca tttcttgag ggatcaggaa ggaatcctgg gtatgccatt gacttccctt | 1200 |
| ctaagtagac agcaaaaatg gcggggtcg caggaatctg cactcaactg cccacctggc | 1260 |
| tggcagggat ctttgaatag gtatcttgag cttggttctg ggctctttcc ttgtgtactg | 1320 |
| acgaccaggg ccagctgttc tagagcggga attagaggct agagcggctg aaatggttgt | 1380 |
| ttggtgatga cactggggtc cttccatctc tggggcccac tctcttctgt cttcccatgg | 1440 |
| gaagtgccac tgggatccct ctgccctgtc ctcctgaata caagctgact gacattgact | 1500 |
| gtgtctgtgg aaaatgggag ctcttgttgt ggagagcata gtaaattttc agagaacttg | 1560 |
| aagccaaaag gatttaaaac cgctgctcta agaaaagaa actggaggc tgggcgcagt | 1620 |
| ggctcacgcc tataatccca gaggctgagg caggcggatc acctgaggtc aggagttcag | 1680 |
| gatcagcctg accaacatgg agaaaccctg ctggaaatac aaagttagcc aggcatggtg | 1740 |
| gtgcatgcct gtagtcccag ctgctcagga gcctggcaac aagagcaaaa ctccagctca | 1800 |
| aaaaaaaaaa aaaaaa | 1816 |

<210> SEQ ID NO 7
<211> LENGTH: 299
<212> TYPE: PRT
<213> ORGANISM: Homo sapiens

<400> SEQUENCE: 7

```
Met Gly Thr Lys Ala Gln Val Glu Arg Lys Leu Leu Cys Leu Phe Ile
1               5                  10                  15

Leu Ala Ile Leu Leu Cys Ser Leu Ala Leu Gly Ser Val Thr Val His
            20                  25                  30

Ser Ser Glu Pro Glu Val Arg Ile Pro Glu Asn Asn Pro Val Lys Leu
        35                  40                  45

Ser Cys Ala Tyr Ser Gly Phe Ser Ser Pro Arg Val Glu Trp Lys Phe
    50                  55                  60

Asp Gln Gly Asp Thr Thr Arg Leu Val Cys Tyr Asn Asn Lys Ile Thr
65                  70                  75                  80

Ala Ser Tyr Glu Asp Arg Val Thr Phe Leu Pro Thr Gly Ile Thr Phe
                85                  90                  95

Lys Ser Val Thr Arg Glu Asp Thr Gly Thr Tyr Thr Cys Met Val Ser
```

```
                100                 105                 110
Glu Glu Gly Gly Asn Ser Tyr Gly Glu Val Lys Val Lys Leu Ile Val
            115                 120                 125

Leu Val Pro Pro Ser Lys Pro Thr Val Asn Ile Pro Ser Ser Ala Thr
        130                 135                 140

Ile Gly Asn Arg Ala Val Leu Thr Cys Ser Glu Gln Asp Gly Ser Pro
145                 150                 155                 160

Pro Ser Glu Tyr Thr Trp Phe Lys Asp Gly Ile Val Met Pro Thr Asn
                165                 170                 175

Pro Lys Ser Thr Arg Ala Phe Ser Asn Ser Ser Tyr Val Leu Asn Pro
            180                 185                 190

Thr Thr Gly Glu Leu Val Phe Asp Pro Leu Ser Ala Ser Asp Thr Gly
        195                 200                 205

Glu Tyr Ser Cys Glu Ala Arg Asn Gly Tyr Gly Thr Pro Met Thr Ser
    210                 215                 220

Asn Ala Val Arg Met Glu Ala Val Glu Arg Asn Val Gly Val Ile Val
225                 230                 235                 240

Ala Ala Val Leu Val Thr Leu Ile Leu Leu Gly Ile Leu Val Phe Gly
                245                 250                 255

Ile Trp Phe Ala Tyr Ser Arg Gly His Phe Asp Arg Thr Lys Lys Gly
                260                 265                 270

Thr Ser Ser Lys Lys Val Ile Tyr Ser Gln Pro Ser Ala Arg Ser Glu
            275                 280                 285

Gly Glu Phe Lys Gln Thr Ser Ser Phe Leu Val
        290                 295

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide primer. A forward
      primer to human F11 receptor cDNA.

<400> SEQUENCE: 8
gcgggatcca tcgcgatggg gacaaaggcg                                       30

<210> SEQ ID NO 9
<211> LENGTH: 36
<212> TYPE: DNA
<213> ORGANISM: Artificial Sequence
<220> FEATURE:
<223> OTHER INFORMATION: Synthetic oligonucletoide primer. A reverse
      primer to human F11 receptor cDNA.

<400> SEQUENCE: 9
ccgacctcga gcggcattcc gctccacagc ttccat                                36

<210> SEQ ID NO 10
<211> LENGTH: 15
<212> TYPE: PRT
<213> ORGANISM: ArtificiaL Sequence
<220> FEATURE:
<223> OTHER INFORMATION: Synthetic peptide

<400> SEQUENCE: 10

Asp Lys Ser Val Thr Asp Arg Glu Asp Thr Gly Thr Tyr Thr Cys
1               5                   10                  15

<210> SEQ ID NO 11
```

```
<211> LENGTH: 14
<212> TYPE: PRT
<213> ORGANISM: Artificial Sequence
<220> FEATURE:
<223> OTHER INFORMATION: Synthetic peptide

<400> SEQUENCE: 11

Lys Ser Val Thr Asp Arg Glu Asp Thr Gly Thr Tyr Thr Cys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic peptide

<400> SEQUENCE: 12

Ser Val Thr Asp Arg Glu Asp Thr Gly Thr Tyr Thr Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Val Thr Asp Arg Glu Asp Thr Gly Thr Tyr Thr Cys
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide

<400> SEQUENCE: 14

Thr Asp Arg Glu Asp Thr Gly Thr Tyr Thr Cys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide

<400> SEQUENCE: 15

Asp Arg Glu Asp Thr Gly Thr Tyr Thr Cys
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Arg Glu Asp Thr Gly Thr Tyr Thr Cys
1               5

<210> SEQ ID NO 17
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 17

Glu Asp Thr Gly Thr Tyr Thr Cys
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Asp Thr Gly Thr Tyr Thr Cys
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Thr Gly Thr Tyr Thr Cys
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic peptide

<400> SEQUENCE: 20

Gly Thr Tyr Thr Cys
1               5

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Asp Lys Ser Val Thr Asp Arg Glu Asp Thr Gly Thr Tyr Thr Cys
1               5                   10                  15

<210> SEQ ID NO 22
<211> LENGTH: 14
<212> TYPE: PRT
<213> ORGANISM: Artificial Sequence
<220> FEATURE:
<223> OTHER INFORMATION: Synthetic peptide

<400> SEQUENCE: 22

Asp Lys Ser Val Thr Asp Arg Glu Asp Thr Gly Thr Tyr Thr
1               5                   10

<210> SEQ ID NO 23
<211> LENGTH: 13
<212> TYPE: PRT
```

<213> ORGANISM: Artificial Sequence
<220> FEATURE:
<223> OTHER INFORMATION: Synthetic peptide

<400> SEQUENCE: 23

Asp Lys Ser Val Thr Asp Arg Glu Asp Thr Gly Thr Tyr
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic peptide

<400> SEQUENCE: 24

Asp Lys Ser Val Thr Asp Arg Glu Asp Thr Gly Thr
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide

<400> SEQUENCE: 25

Asp Lys Ser Val Thr Asp Arg Glu Asp Thr Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic peptide

<400> SEQUENCE: 26

Asp Lys Ser Val Thr Asp Arg Glu Asp Thr
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Asp Lys Ser Val Thr Asp Arg Glu Asp
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide

<400> SEQUENCE: 28

Asp Lys Ser Val Thr Asp Arg Glu
1               5

<210> SEQ ID NO 29
<211> LENGTH: 7
<212> TYPE: PRT
<213> ORGANISM: Artificial Sequence

```
<220> FEATURE:
<223> OTHER INFORMATION: Synthetic peptide

<400> SEQUENCE: 29

Asp Lys Ser Val Thr Asp Arg
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide

<400> SEQUENCE: 30

Asp Lys Ser Val Thr Asp
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide

<400> SEQUENCE: 31

Asp Lys Ser Val Thr
1               5

<210> SEQ ID NO 32
<211> LENGTH: 22
<212> TYPE: PRT
<213> ORGANISM: Artificial Sequence
<220> FEATURE:
<223> OTHER INFORMATION: Synthetic peptide

<400> SEQUENCE: 32

Val Thr Val His Ser Ser Glu Pro Glu Val Arg Ile Pro Glu Asn Asn
1               5                   10                  15

Pro Val Lys Leu Ser Cys
            20

<210> SEQ ID NO 33
<211> LENGTH: 21
<212> TYPE: PRT
<213> ORGANISM: Artificial Sequence
<220> FEATURE:
<223> OTHER INFORMATION: Synthetic peptide

<400> SEQUENCE: 33

Thr Val His Ser Ser Glu Pro Glu Val Arg Ile Pro Glu Asn Asn Pro
1               5                   10                  15

Val Lys Leu Ser Cys
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic peptide

<400> SEQUENCE: 34

Val His Ser Ser Glu Pro Glu Val Arg Ile Pro Glu Asn Asn Pro Val
1               5                   10                  15
```

```
Lys Leu Ser Cys
            20

<210> SEQ ID NO 35
<211> LENGTH: 19
<212> TYPE: PRT
<213> ORGANISM: Artificial Sequence
<220> FEATURE:
<223> OTHER INFORMATION: Synthetic peptide

<400> SEQUENCE: 35

His Ser Ser Glu Pro Glu Val Arg Ile Pro Glu Asn Asn Pro Val Lys
1               5                   10                  15

Leu Ser Cys

<210> SEQ ID NO 36
<211> LENGTH: 18
<212> TYPE: PRT
<213> ORGANISM: Artificial Sequence
<220> FEATURE:
<223> OTHER INFORMATION: Synthetic peptide

<400> SEQUENCE: 36

Ser Ser Glu Pro Glu Val Arg Ile Pro Glu Asn Asn Pro Val Lys Leu
1               5                   10                  15

Ser Cys

<210> SEQ ID NO 37
<211> LENGTH: 17
<212> TYPE: PRT
<213> ORGANISM: Artificial Sequence
<220> FEATURE:
<223> OTHER INFORMATION: Synthetic peptide

<400> SEQUENCE: 37

Ser Glu Pro Glu Val Arg Ile Pro Glu Asn Asn Pro Val Lys Leu Ser
1               5                   10                  15

Cys

<210> SEQ ID NO 38
<211> LENGTH: 16
<212> TYPE: PRT
<213> ORGANISM: Artificial Sequence
<220> FEATURE:
<223> OTHER INFORMATION: Synthetic peptide

<400> SEQUENCE: 38

Glu Pro Glu Val Arg Ile Pro Glu Asn Asn Pro Val Lys Leu Ser Cys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic peptide

<400> SEQUENCE: 39

Pro Glu Val Arg Ile Pro Glu Asn Asn Pro Val Lys Leu Ser Cys
1               5                   10                  15

<210> SEQ ID NO 40
<211> LENGTH: 14
<212> TYPE: PRT
<213> ORGANISM: Artificial Sequence
```

<220> FEATURE:
<223> OTHER INFORMATION: Synthetic peptide

<400> SEQUENCE: 40

Glu Val Arg Ile Pro Glu Asn Asn Pro Val Lys Leu Ser Cys
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthetic peptide

<400> SEQUENCE: 41

Val Arg Ile Pro Glu Asn Asn Pro Val Lys Leu Ser Cys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic peptide

<400> SEQUENCE: 42

Arg Ile Pro Glu Asn Asn Pro Val Lys Leu Ser Cys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic peptide

<400> SEQUENCE: 43

Ile Pro Glu Asn Asn Pro Val Lys Leu Ser Cys
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic peptide

<400> SEQUENCE: 44

Pro Glu Asn Asn Pro Val Lys Leu Ser Cys
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Glu Asn Asn Pro Val Lys Leu Ser Cys
1               5

<210> SEQ ID NO 46
<211> LENGTH: 8
<212> TYPE: PRT
<213> ORGANISM: Artificial Sequence
<220> FEATURE:

<223> OTHER INFORMATION: Synthetic peptide

<400> SEQUENCE: 46

Asn Asn Pro Val Lys Leu Ser Cys
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

Asn Pro Val Lys Leu Ser Cys
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic peptide

<400> SEQUENCE: 48

Pro Val Lys Leu Ser Cys
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic peptide

<400> SEQUENCE: 49

Val Lys Leu Ser Cys
1               5

<210> SEQ ID NO 50
<211> LENGTH: 22
<212> TYPE: PRT
<213> ORGANISM: Artificial Sequence
<220> FEATURE:
<223> OTHER INFORMATION: Synthetic peptide

<400> SEQUENCE: 50

Ser Val Thr Val His Ser Ser Glu Pro Glu Val Arg Ile Pro Glu Asn
1               5                   10                  15

Asn Pro Val Lys Leu Ser
            20

<210> SEQ ID NO 51
<211> LENGTH: 21
<212> TYPE: PRT
<213> ORGANISM: Artificial Sequence
<220> FEATURE:
<223> OTHER INFORMATION: Synthetic peptide

<400> SEQUENCE: 51

Ser Val Thr Val His Ser Ser Glu Pro Glu Val Arg Ile Pro Glu Asn
1               5                   10                  15

Asn Pro Val Lys Leu
            20

```
<210> SEQ ID NO 52
<211> LENGTH: 20
<212> TYPE: PRT
<213> ORGANISM: Artificial Sequence
<220> FEATURE:
<223> OTHER INFORMATION: Synthetic peptide

<400> SEQUENCE: 52

Ser Val Thr Val His Ser Ser Glu Pro Glu Val Arg Ile Pro Glu Asn
1               5                   10                  15

Asn Pro Val Lys
            20

<210> SEQ ID NO 53
<211> LENGTH: 19
<212> TYPE: PRT
<213> ORGANISM: Artificial Sequence
<220> FEATURE:
<223> OTHER INFORMATION: Synthetic peptide

<400> SEQUENCE: 53

Ser Val Thr Val His Ser Ser Glu Pro Glu Val Arg Ile Pro Glu Asn
1               5                   10                  15

Asn Pro Val

<210> SEQ ID NO 54
<211> LENGTH: 18
<212> TYPE: PRT
<213> ORGANISM: Artificial Sequence
<220> FEATURE:
<223> OTHER INFORMATION: Synthetic peptide

<400> SEQUENCE: 54

Ser Val Thr Val His Ser Ser Glu Pro Glu Val Arg Ile Pro Glu Asn
1               5                   10                  15

Asn Pro

<210> SEQ ID NO 55
<211> LENGTH: 17
<212> TYPE: PRT
<213> ORGANISM: Artificial Sequence
<220> FEATURE:
<223> OTHER INFORMATION: Synthetic peptide

<400> SEQUENCE: 55

Ser Val Thr Val His Ser Ser Glu Pro Glu Val Arg Ile Pro Glu Asn
1               5                   10                  15

Asn

<210> SEQ ID NO 56
<211> LENGTH: 16
<212> TYPE: PRT
<213> ORGANISM: Artificial Sequence
<220> FEATURE:
<223> OTHER INFORMATION: Synthetic peptide

<400> SEQUENCE: 56

Ser Val Thr Val His Ser Ser Glu Pro Glu Val Arg Ile Pro Glu Asn
1               5                   10                  15

<210> SEQ ID NO 57
<211> LENGTH: 15
<212> TYPE: PRT
<213> ORGANISM: Artificial Sequence
<220> FEATURE:
```

<223> OTHER INFORMATION: Synthetic peptide

<400> SEQUENCE: 57

Ser Val Thr Val His Ser Ser Glu Pro Glu Val Arg Ile Pro Glu
1               5                   10                  15

<210> SEQ ID NO 58
<211> LENGTH: 14
<212> TYPE: PRT
<213> ORGANISM: Artificial Sequence
<220> FEATURE:
<223> OTHER INFORMATION: Synthetic peptide

<400> SEQUENCE: 58

Ser Val Thr Val His Ser Ser Glu Pro Glu Val Arg Ile Pro
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Synthetic peptide

<400> SEQUENCE: 59

Ser Val Thr Val His Ser Ser Glu Pro Glu Val Arg Ile
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthetic peptide

<400> SEQUENCE: 60

Ser Val Thr Val His Ser Ser Glu Pro Glu Val Arg
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Synthetic peptide

<400> SEQUENCE: 61

Ser Val Thr Val His Ser Ser Glu Pro Glu Val
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Synthetic peptide

<400> SEQUENCE: 62

Ser Val Thr Val His Ser Ser Glu Pro Glu
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 63

Ser Val Thr Val His Ser Ser Glu Pro
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic peptide

<400> SEQUENCE: 64

Ser Val Thr Val His Ser Ser Glu
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic peptide

<400> SEQUENCE: 65

Ser Val Thr Val His Ser Ser Glu
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic peptide

<400> SEQUENCE: 66

Ser Val Thr Val His Ser Ser
1               5

<210> SEQ ID NO 67
<211> LENGTH: 6
<212> TYPE: PRT
<213> ORGANISM: Artificial Sequence
<220> FEATURE:
<223> OTHER INFORMATION: Synethetic peptide

<400> SEQUENCE: 67

Ser Val Thr Val His Ser
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic peptide

<400> SEQUENCE: 68

Ser Val Thr Val His
1               5
```